US009834512B2

(12) United States Patent
DeLuca et al.

(10) Patent No.: US 9,834,512 B2
(45) Date of Patent: Dec. 5, 2017

(54) (22E)-2-METHYLENE-26,27-CYCLO-22-DEHYDRO-1α-HYDROXY-19-NORVITAMIN $D_3$ DERIVATIVES

(75) Inventors: Hector DeLuca, Deerfield, WI (US); Rafal Barycki, Madison, WI (US); Lori Plum, Arena, WI (US); Margaret Clagett-Dame, Deerfield, WI (US)

(73) Assignee: WISCONSIN ALUMNI RESEARCH FOUNDATION, Madison, WI (US)

(*) Notice: Subject to any disclaimer, the term of this patent is extended or adjusted under 35 U.S.C. 154(b) by 818 days.

(21) Appl. No.: 13/485,343

(22) Filed: May 31, 2012

(65) Prior Publication Data

US 2012/0309719 A1 Dec. 6, 2012

Related U.S. Application Data

(60) Provisional application No. 61/493,079, filed on Jun. 3, 2011.

(51) Int. Cl.
*A61K 31/59* (2006.01)
*C07C 401/00* (2006.01)

(52) U.S. Cl.
CPC ........ *C07C 401/00* (2013.01); *C07C 2601/02* (2017.05); *C07C 2601/14* (2017.05); *C07C 2602/24* (2017.05)

(58) Field of Classification Search
CPC .............. C07C 401/00; C07C 2601/02; C07C 2601/14; C07C 2602/24
USPC ........................................... 552/653; 514/167
See application file for complete search history.

(56) References Cited

U.S. PATENT DOCUMENTS

| | | | |
|---|---|---|---|
| 4,666,634 | A | 5/1987 | Miyamoto et al. |
| 5,063,221 | A | 11/1991 | Nishii et al. |
| 5,086,191 | A | 2/1992 | DeLuca et al. |
| 5,246,925 | A | 9/1993 | DeLuca et al. |
| 5,536,713 | A | 7/1996 | Deluca et al. |
| 5,545,633 | A | 8/1996 | Bretting |
| 5,585,369 | A | 12/1996 | DeLuca et al. |
| 5,587,497 | A | 12/1996 | DeLuca et al. |
| 5,843,928 | A | 12/1998 | Deluca et al. |
| 5,929,056 | A | 7/1999 | Mourino et al. |
| 5,936,133 | A | 8/1999 | Deluca et al. |
| 5,945,410 | A | 8/1999 | DeLuca et al. |
| 6,376,480 | B1 | 4/2002 | Kirsch et al. |
| 6,399,797 | B1 | 6/2002 | von Daehne et al. |
| 6,537,981 | B2 | 3/2003 | DeLuca et al. |
| 6,566,352 | B1 | 5/2003 | DeLuca et al. |
| 6,579,861 | B2 | 6/2003 | DeLuca et al. |
| 6,627,622 | B2 | 9/2003 | DeLuca et al. |
| 6,703,380 | B2 | 3/2004 | Raskov |
| 7,208,484 | B2 | 4/2007 | DeLuca et al. |
| 7,232,810 | B2 | 6/2007 | DeLuca et al. |
| 7,713,953 | B2 | 5/2010 | DeLuca et al. |
| 7,915,242 | B2 | 3/2011 | DeLuca et al. |
| 2003/0018194 | A1 | 1/2003 | Steinmeyer et al. |

(Continued)

FOREIGN PATENT DOCUMENTS

| | | |
|---|---|---|
| WO | WO-97/00242 | 1/1997 |

OTHER PUBLICATIONS

International Preliminary Report on Patentability for Intl. Pat. Appln. No. PCT/US2012/040235, dated Dec. 4, 2013, 11 pp.

(Continued)

*Primary Examiner* — Barbara P Badio
(74) *Attorney, Agent, or Firm* — Foley & Lardner LLP

(57) ABSTRACT

Cyclopropane-containing vitamin D analogs of formulas I and IV are provided. Such compounds may be used in preparing pharmaceutical compositions and are useful in treating a variety of biological conditions.

I

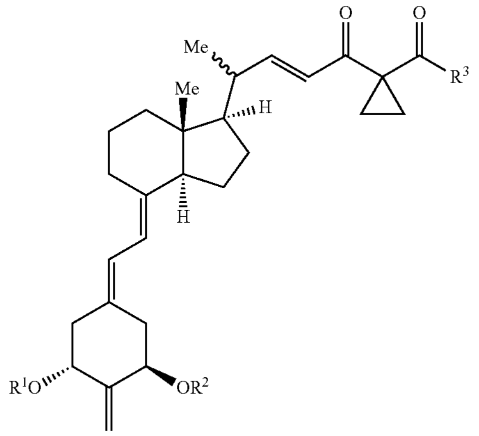

IV

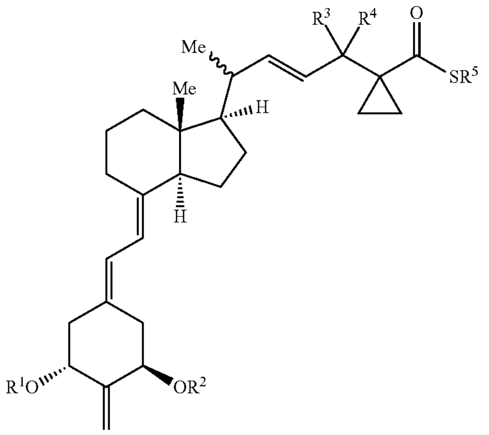

16 Claims, 10 Drawing Sheets

(56) References Cited

U.S. PATENT DOCUMENTS

2005/0080059 A1 4/2005 DeLuca et al.
2005/0182033 A1 8/2005 DeLuca et al.
2008/0261925 A1 10/2008 Clagett-Dame et al.

OTHER PUBLICATIONS

Arbour, Nancy C. et al., "A Highly Sensitive Method for Large-Scale Measurements of 1,25-Dihydroxyvitamin D," Analytical Biochemistry, vol. 255, (1998), pp. 148-154.
Baggiolini, Enrico G. et al., Stereocontrolled Total Synthesis of 1α,25-Dihydroxycholecalciferol(1) and 1α,25-Dihydroxyergocalciferol, J. Org. Chem., 51, (1986), pp. 3098-3108.
Collins, S.J. et al., "Normal Functional Characteristics of Cultured Human Promyelocytic Leukemia Cells (HL-60) After Induction of Differentiation by Dimethylsulfoxide" J. Exp. Med., vol. 149, (1979), pp. 969-974.
Greene, T.W. et al., "Protection for the Hydroxyl Group, Including 1,2- and 1,3-Diols", Protective Groups in Organic Synthesis, Third Edition, John Wiley & Sons, Inc., (1999), pp. 17-245.
Lythgoe, B. et al., "Synthetic Approaches to Vitamin D and its Relatives," Chem. Soc. Rev. 9, (1983), p. 449-475.
Lythgoe, Basil et al., "Calciferol and its relatives. Part 22. A direct total synthesis of vitamin $D_2$ and vitamin $D_3$," J. Chem. Soc., Perkin Trans. 1, (1978), pp. 590-595.
Mascarenas, J. L. et al., "Studies on the Synthesis of Side-Chain Hydroxylated Metabolites of Vitamin D. 3. Synthesis of 25-Ketovitamin $D_3$ and 25-Hydroxyvitamin $D_3^1$," J. Org. Chem., vol. 51, (1986), pp. 1269-1272.
Mincione, E. et al., "Improved Conversion of Vitamin $D_2$ into the Windaus Ketone and its Regioselective Hydroxylation via Organoboranes at $C_{26}$," Synthetic Communications, vol. 19 Nos. 5-6, (1989), pp. 723-735.
Ostrem, Voula K. et al., "24- and 26-homo-1,25-dihydroxyvitamin $D_3$: Preferential activity in inducing differentiation of human leukemia cells HL-60 in vitro," Proc. Natl. Acad. Sci. USA, vol. 84, (May 1987), pp. 2610-2614.
Perlman, Kato L. et al., "Novel Synthesis of 19-Nor-Vitamin D Compounds," Tetrahedron Letters, vol. 32, No. 52, (1991), pp. 7663-7666.
Peterson, Paul E. et al., "Studies of the Ketone Obtained from the Ozonolysis of Vitamin D. Molecular Mechanics Calculations for It and Related Hydrindanones," J. Org. Chem., 51 (11), (1986), pp. 1948-1954.
Sardina, F. Javier et al., "Studies on the Synthesis of Side-Chain Hydroxylated Metabolites of Vitamin D. 2. Stereocontrolled Synthesis of 25-Hydroxyvitamin $D_2$," J. Org. Chem., 51, (1986), pp. 1264-1269.
Sicinski, Rafal R. et al., "New 1α,25-Dihydroxy-19-norvitamin $D_3$ Compounds of High Biological Activity: Synthesis and Biological Evaluation of 2-Hydroxymethyl, 2-Methyl, and 2-Methylene Analogues," J. Med. Chem., 41, (1998), pp. 4662-4674.
Toh, H.T. et al., "Studies on a Convergent Route to Side-Chain Analogues of Vitamin D: 25-Hydroxy-23-oxavitamin $D_3$," J. Org. Chem., 48, (1983), pp. 1414-1417.
International Search Report and Written Opinion for Intl. Pat. Appln. No. PCT/US2012/040235, dated Dec. 10, 2012 , 17 pp.
Binderup, Lise et al., "Effects of a Novel Vitamin D Analogue MC903 on Cell Proliferation and Differentiation In Vitro and on Calcium Metabolism In Vivo," Biochemical Pharmacology, (1988), vol. 37, No. 5, pp. 889-895.
Campbell, Moray J. et al., "Toward Therapeutic Intervention of Cancer by Vitamin D Compounds," Journal of the National Cancer Institute, (Feb. 5, 1997), vol. 89, No. 3, pp. 182-185.
Cantorna, Margherita T. et al., "1,25 Dihydroxyvitamin D3 Reversibly Blocks the Progression of Relapsing Encephalomyelitis, a Model of Multiple Sclerosis," Proc. Natl. Acad. Sci. USA, (Jul. 1996), vol. 93, pp. 7861-7864.
DeLuca, H. F., "Applications of New Vitamin D. Compounds to Disease," DN&P,(Mar. 1992), vol. 5, No. 2, pp. 87-92.
Gallagher, J.C. et al., "Effects of Calcitriol in Osteoporosis," Osteoporosis: Recent Advanced in Pathogenesis and Treatment, University Park Press, Baltimore, Maryland, (1981), pp. 419-423.
Plum, Lori A., et al., "Biologically active noncalcemic analogs of 1alpha,25-dihydroxyvitamin D with an abbreviated side chain containing no hydroxyl," Proceedings of the National Academy of Science, May 2004, vol. 101, No. 18, pp. 6900-6904.
Rebel, Vivienne I. et al., "Monocytic Differentiation Induction of HL-60 Cells by MC 903, a Novel Vitamin D Analogue," Leukemia Research, (1992), vol. 16, No. 5, pp. 443-451.
Shiraki, Masataka et al., "Long-Term Treatment of Postmenopausal Osteoporosis with Active Vitamin D3, 1-α-Hydroxycholecalciferol (1α-OHD3) and 1,24 Dihydroxycholecalciferol (1,24(OH)2D3)," Endocrinol. Japon., (Apr. 1985), 32(2), pp. 305-315.

$K_i$: $1,25(OH)_2D_3 = 1 \times 10^{-10}$ M
2MD = $2 \times 10^{-10}$ M
PP-48 = $6 \times 10^{-10}$ M $K_i$: $1,25(OH)_2D_3 = 1 \times 10^{-10}$ M AS-51 = $1 \times 10^{-10}$ M EC50: $1,25(OH)_2D_3 = 2 \times 10^{-9}$ M

AS-51 = $>10^{-6}$ M $1,25(OH)_2D_3$ + AS-51 @ $10^{-9}$ M = $2 \times 10^{-9}$ M $1,25(OH)_2D_3$ + AS-51 @ $10^{-8}$ M = $1 \times 10^{-8}$ M $1,25(OH)_2D_3$ + AS-51 @ $10^{-7}$ M = $>10^{-8}$ M $1,25(OH)_2D_3$ + AS-51 @ $10^{-6}$ M = $>10^{-7}$ M $EC_{50}$: $1{,}25(OH)_2D_3 = 1 \times 10^{-10}$ M AS-51 = $6 \times 10^{-9}$ M $1{,}25(OH)_2D_3$ + AS-51 @ $10^{-9}$ M = $4 \times 10^{-10}$ M $1{,}25(OH)_2D_3$ + AS-51 @ $10^{-8}$ M = $4 \times 10^{-9}$ M $1{,}25(OH)_2D_3$ + AS-51 @ $10^{-7}$ M = $2 \times 10^{-8}$ M

(22E)-2-METHYLENE-26,27-CYCLO-22-DEHYDRO-1α-HYDROXY-19-NORVITAMIN $D_3$ DERIVATIVES

CROSS-REFERENCE TO RELATED PATENT APPLICATIONS

This application claims priority to U.S. Provisional Application No. 61/493,079, filed Jun. 3, 2011, the entire disclosure of which is hereby incorporated by reference and for all purposes in its entirety as if fully set forth herein.

FIELD

This present technology relates to vitamin D compounds, and more particularly to (22E)-2-methylene-25-alkanoyl-24-oxo-26,27-cyclo-22-dehydro-1α-hydroxy-19-norvitamin $D_3$, (22E)-25-carboalkylsulfanyl-2-methylene-26,27-cyclo-22-dehydro-24-oxo-1α-hydroxy-19-norvitamin $D_3$, (22E)-25-carbobutylsulfanyl-2-methylene-26,27-cyclo-22-dehydro-1α,24-dihydroxy-19-norvitamin $D_3$ and derivatives thereof, and to pharmaceutical formulations that include these compounds. The present technology also relates to the use of these compounds in the treatment of various diseases and in the preparation of medicaments for use in treating various diseases.

BACKGROUND

The natural hormone, 1α,25-dihydroxyvitamin $D_3$ (also referred to as 1α,25-dihydroxycholecalciferol and calcitriol) and its analog in the ergosterol series, i.e., 1α,25-dihydroxyvitamin $D_2$, are known to be highly potent regulators of calcium homeostasis in animals and humans, and their activity in cellular differentiation has also been established, Ostrem et al., *Proc. Natl. Acad. Sci. USA,* 84, 2610 (1987). Many structural analogs of these metabolites have been prepared and tested, including 1α-hydroxyvitamin $D_3$, 1α-hydroxyvitamin $D_2$, various side chain homologated vitamins, and fluorinated analogs. Some of these compounds exhibit an interesting separation of activities in cell differentiation and calcium regulation. This difference in activity may be useful in the treatment of a variety of diseases as renal osteodystrophy, vitamin D-resistant rickets, osteoporosis, psoriasis, and certain malignancies. The structure of 1α,25-dihydroxyvitamin $D_3$ and the numbering system used to denote the carbon atoms in this compound are shown below.

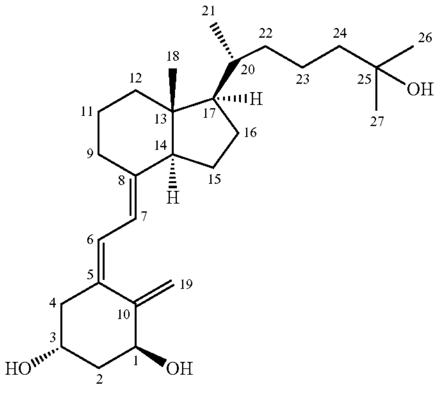

1α, 25-Dihydroxyvitamin $D_3$ = 1, $25(OH)_2D_3$ = 1α, 25- Dihydroxycholecalciferol = Calcitriol

SUMMARY

The present technology provides diastereomers of (22E)-2-methylene-25-alkanoyl-24-oxo-26,27-cyclo-22-dehydro-1α-hydroxy-19-norvitamin $D_3$, and related compounds, pharmaceutical formulations that include a diastereomer of (22E)-2-methylene-25-alkanoyl-24-oxo-26,27-cyclo-22-dehydro-1α-hydroxy-19-norvitamin $D_3$, methods of treating various disease states using these compounds, and the use of these compounds in the preparation of medicaments for treating various disease states. The present technology also provides diastereomers of (22E)-25-carboalkylsulfanyl-2-methylene-26,27-cyclo-22-dehydro-24-oxo-1α-hydroxy-19-norvitamin $D_3$ as well as diastereomers of (22E)-25-carbobutylsulfanyl-2-methylene-26,27-cyclo-22-dehydro-1α,24-dihydroxy-19-norvitamin $D_3$, and related compounds, pharmaceutical formulations that include a diastereomer of (22E)-25-carboalkylsulfanyl-2-methylene-26,27-cyclo-22-dehydro-24-oxo-1α-hydroxy-19-norvitamin $D_3$ or (22E)-25-carbobutylsulfanyl-2-methylene-26,27-cyclo-22-dehydro-1α,24-dihydroxy-19-norvitamin $D_3$, methods of treating various disease states using these compounds, and the use of these compounds in the preparation of medicaments for treating various disease states.

Therefore, in one aspect, the present technology provides a compound having the formula I shown below, or a pharmaceutically acceptable salt thereof,

I

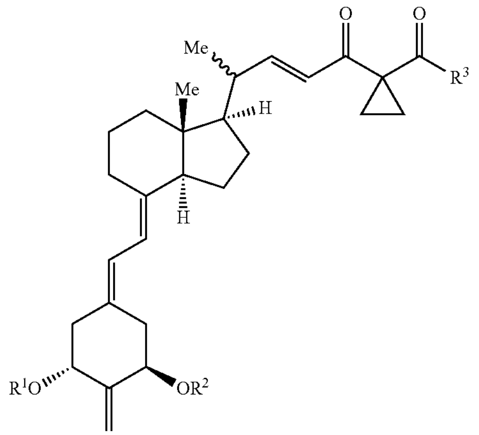

where $R^1$ and $R^2$ are independently selected from H and hydroxy protecting groups; and $R^3$ is a straight or branched chain alkyl group having 1 to 8 carbon atoms. In some embodiments $R^3$ is isopentyl. In others, $R^3$ is methyl, ethyl, propyl, n-propyl, isopropyl, butyl, n-butyl, sec-butyl, isobutyl, pentyl, n-pentyl, isopentyl, 2,2-dimethylpropyl, hexyl, n-hexyl, 2-methyl-pentyl, 3-methylpentyl, 2,2-dimethylbutyl, 2,3-dimethylbutyl, or the like. In other embodiments, $R^1$ and $R^2$ are hydroxy protecting groups such as silyl protecting groups. In some such embodiments, $R^1$ and $R^2$ are both t-butyldimethylsilyl groups. In some embodiments, the carbon at position 20 has the R configuration as shown in the compound of formula IA. In other embodiments, the carbon at position 20 has the S configuration as shown in the compound of formula IB.

IA

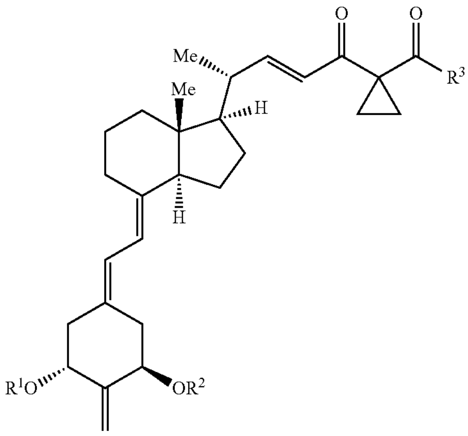

IB

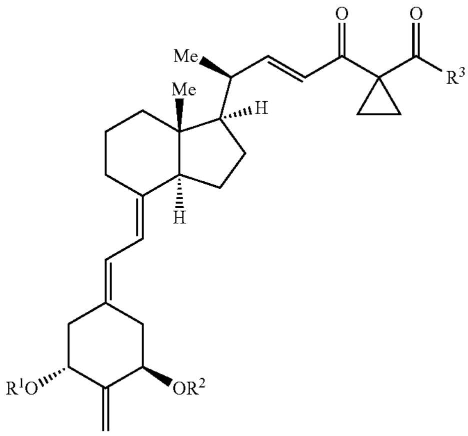

In other embodiments, $R^1$ and $R^2$ are H such that the compound has the formula II.

II

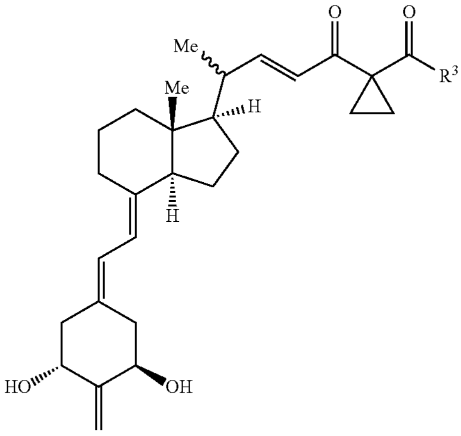

In some such embodiments, the configuration of the carbon at the 20 position has an R or S configuration such that the compound has the formula IIA or IIB.

IIA

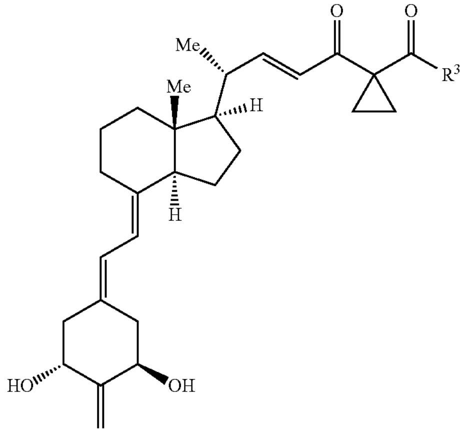

IIB

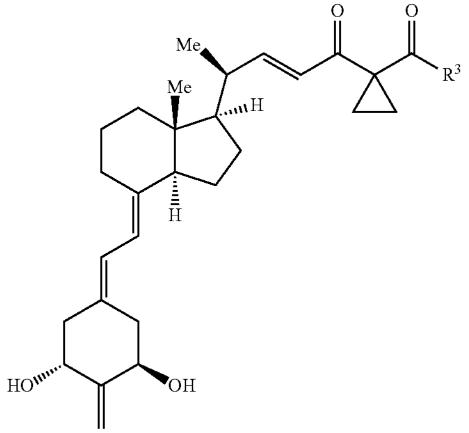

In some embodiments, the compound is (20R,22E)-2-methylene-25-(4-methylpentanoyl)-24-oxo-26,27-cyclo-22-dehydro-1α-hydroxy-19-norvitamin $D_3$ (also known as PP-48) and has the formula IIIA as shown below or (20S,22E)-2-methylene-25-(4-methylpentanoyl)-24-oxo-26,27-cyclo-22-dehydro-1α-hydroxy-19-norvitamin $D_3$ and has the formula IIIB as shown below.

IIIA

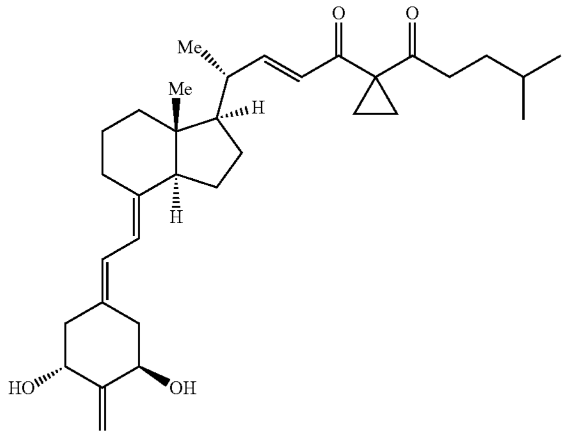

-continued

IIIB

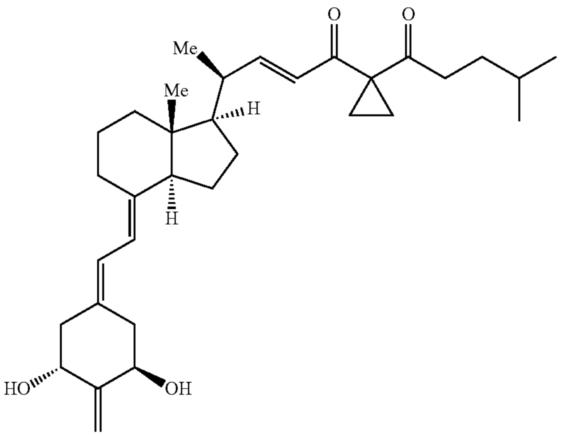

Compounds of formula I, IA, IB, IIA, IIB, IIIA, and IIIB display highly advantageous pattern of biological activity, including binding to the vitamin D receptor and selective action on intestinal calcium transport. Thus, such compounds may be used in methods of treating a subject suffering from certain biological conditions. The methods include administering an effective amount of the compound or a pharmaceutical composition comprising an effective amount of the compound to the subject, where the biological condition is selected from psoriasis; leukemia; colon cancer; breast cancer; prostate cancer; multiple sclerosis; lupus; diabetes mellitus; host versus graft reaction; rejection of organ transplants; an inflammatory disease selected from rheumatoid arthritis, asthma, or inflammatory bowel diseases; a skin condition selected from wrinkles, lack of adequate skin firmness, lack of adequate dermal hydration, or insufficient sebum secretion; renal osteodystrophy; or osteoporosis Compounds of formula I, IA, IB, IIA, IIB, IIIA, and IIIB may be present in a composition to treat the above-noted diseases and disorders in an effective amount and optionally including a pharmaceutically acceptable carrier. In some embodiments, the amount of compound includes from about 0.01 µg per gram of composition to about 1 mg per gram of the composition, preferably from about 0.1 µg per gram to about 500 µg per gram of the composition, and may be administered topically, transdermally, orally, or parenterally in dosages of from about 0.01 µg per day to about 1 mg per day, preferably from about 0.1 µg per day to about 500 µg per day.

In another aspect, the present technology provides a compound having the formula IV shown below or a pharmaceutically acceptable salt thereof,

IV

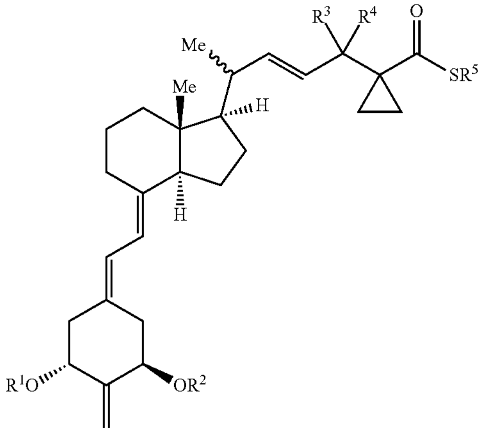

where $R^1$ and $R^2$ are independently selected from H and hydroxy protecting groups; $R^3$ is $OR^6$ and $R^4$ is H, where $R^6$ is H or a hydroxy protecting group; or $R^3$ and $R^4$ together represent a =O group; and $R^5$ is a straight or branched chain alkyl group having 1 to 8 carbon atoms. In certain embodiments, $R^5$ is methyl, ethyl, propyl, n-propyl, isopropyl, butyl, n-butyl, sec-butyl, isobutyl, t-butyl, pentyl, n-pentyl, isopentyl, 2,2-dimethylpropyl, hexyl, n-hexyl, 2-methylpentyl, 3-methylpentyl, 2,2-dimethylbutyl, 2,3-dimethylbutyl, or the like. In some embodiments, $R^3$ is $OR^6$ and $R^4$ is H, where $R^6$ is hydroxy protecting group such as a silyl group, e.g., a triethylsilyl group. In other embodiments, $R^3$ is a hydroxyl group and $R^4$ is H. In other embodiments, $R^3$ and $R^4$ together represent a =O group. In some embodiments, $R^1$ and $R^2$ are hydroxy protecting groups such as silyl protecting groups. In some such embodiments, $R^1$ and $R^2$ are both t-butyldimethylsilyl groups. In some embodiments, the carbon at position 20 has the R configuration as shown in the compound of formula IVA. In other embodiments, the carbon at position 20 has the S configuration as shown in the compound of formula IVB.

IVA

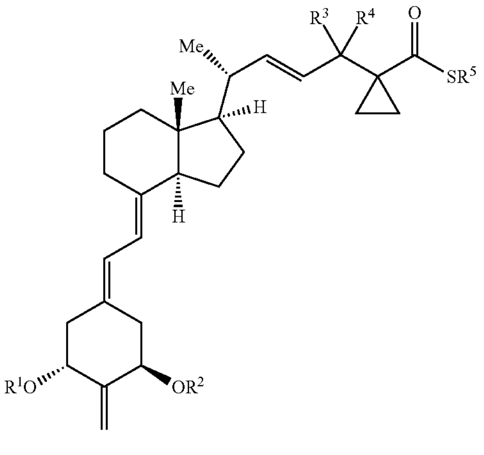

-continued
IVB
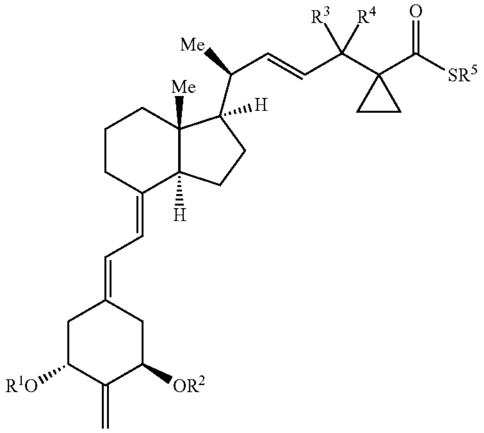
In other embodiments, $R^1$ and $R^2$ are H, $R^3$ is a hydroxyl group, $R^4$ is H, or $R^1$ and $R^2$ are H and $R^3$ and $R^4$ together represent a =O group such that the compound has a formula VA, VB, VIA, VIB, VIC, or VID.
VA
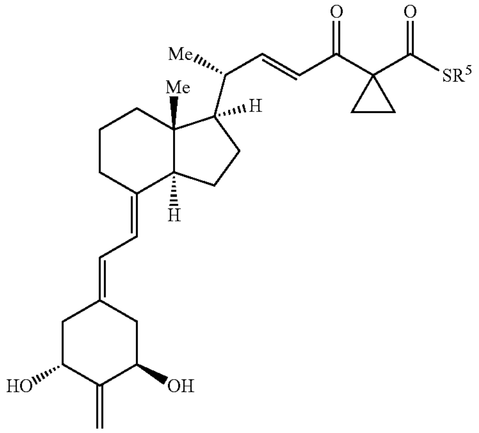
VB
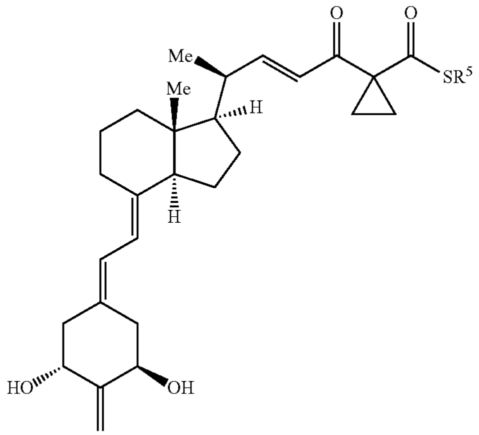
-continued
VIA
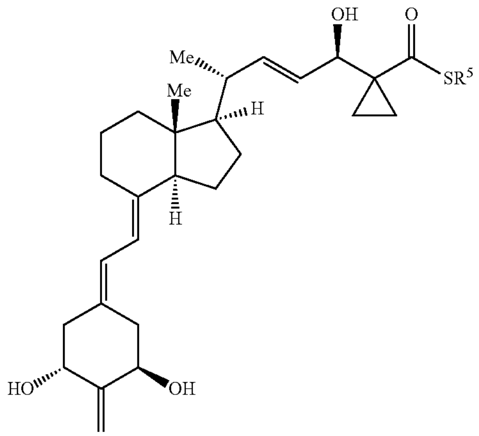
VIB
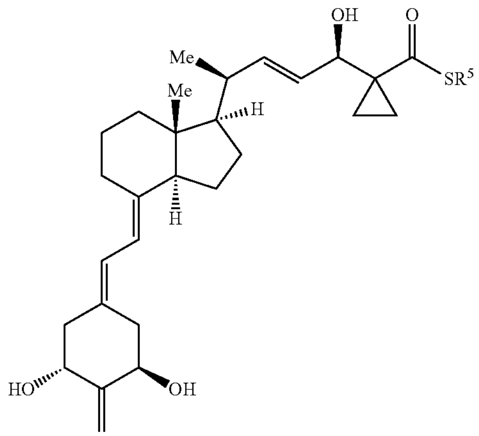
VIC
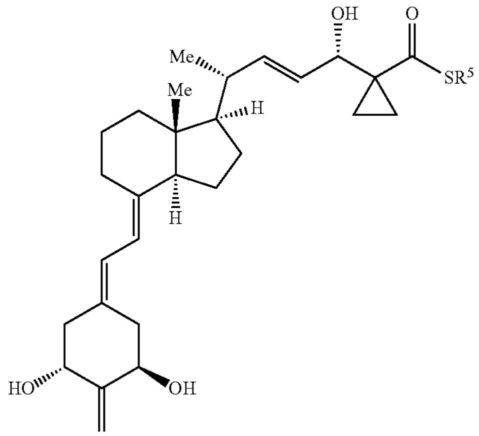

-continued

VID

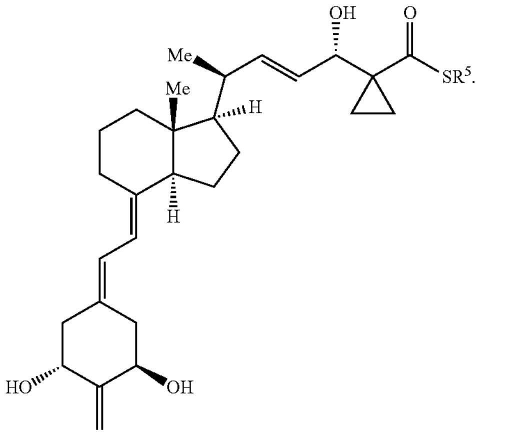

In some embodiments, $R^1$ and $R^2$ are H, $R^3$ and $R^4$ together represent a =O group, and $R^5$ is a butyl group or $R^1$ and $R^2$ are H, $R^3$ is a hydroxyl group, $R^4$ is H, and $R^5$ is a butyl group, such that the compound is (20R,22E)-25-carbobutylsulfanyl-2-methylene-26,27-cyclo-22-dehydro-24-oxo-1α-hydroxy-19-norvitamin $D_3$ and has the formula VIIA, (20S,22E)-25-carbobutylsulfanyl-2-methylene-26,27-cyclo-22-dehydro-24-oxo-1α-hydroxy-19-norvitamin $D_3$ and has the formula VIIB, (20R,22E,24R)-25-carbobutylsulfanyl-2-methylene-26,27-cyclo-22-dehydro-1α,24-dihydroxy-19-norvitamin $D_3$ (also known as AS-51) and has the formula VIIIA, (20S,22E,24R)-25-carbobutylsulfanyl-2-methylene-26,27-cyclo-22-dehydro-1α,24-dihydroxy-19-norvitamin $D_3$ and has the formula VIIIB, (20R,22E,24S)-25-carbobutylsulfanyl-2-methylene-26,27-cyclo-22-dehydro-1α,24-dihydroxy-19-norvitamin $D_3$ and has the formula VIIIC, or (20S,22E,24S)-25-carbobutylsulfanyl-2-methylene-26,27-cyclo-22-dehydro-1α,24-dihydroxy-19-norvitamin $D_3$ and has the formula VIIID as shown below.

VIIA

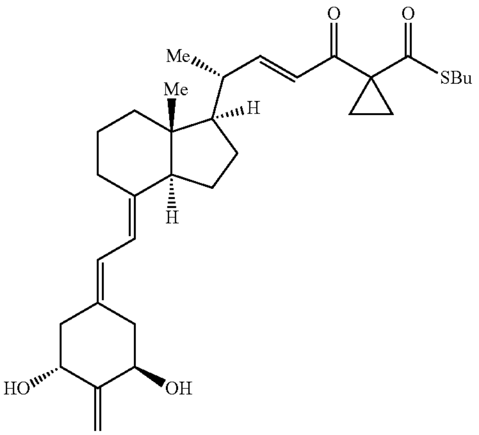

-continued

VIIB

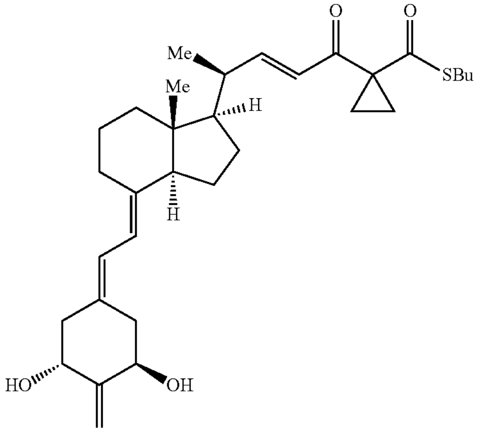

VIIIA

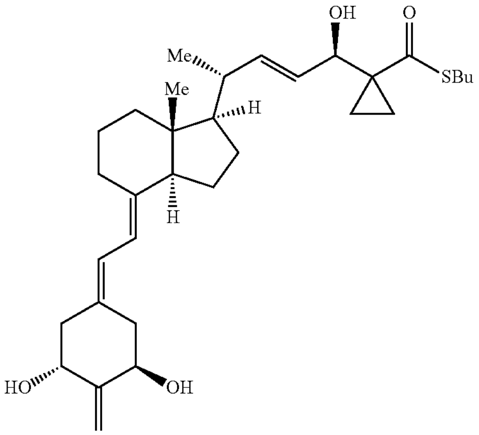

VIIIB

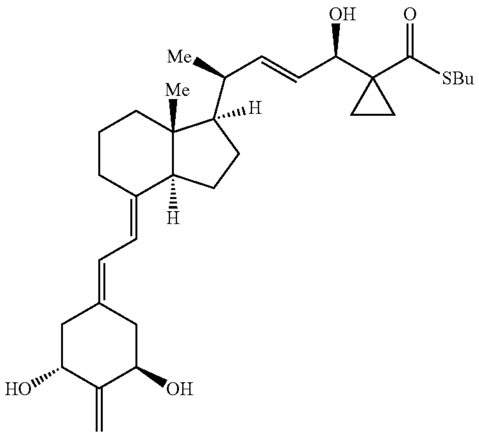

-continued

VIIIC

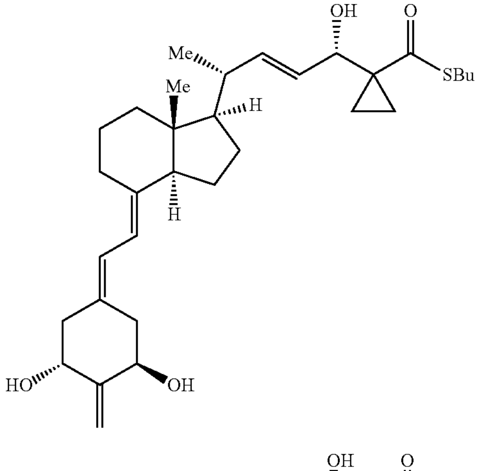

VIIID

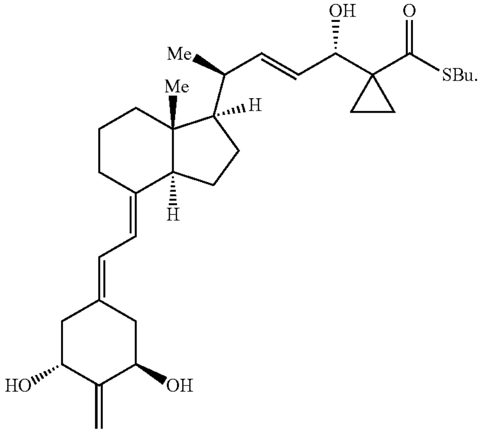

Compounds of formula IV, IVA, IVB, VA, VB, VIA, VIB, VIC, VID, VIIA, VIIB, VIIIA, VIIIB, VIIIC, and VIIID display highly advantageous pattern of biological activity, including antagonizing the vitamin D receptor. Thus, such compounds may be used in methods of treating a subject suffering from certain biological conditions. In one aspect, a method of antagonizing the vitamin D receptor is provided, the method including administering an effective amount of a compound of the present technology or a pharmaceutical composition comprising an effective amount of such a compound to a subject, where the compound administered to the subject antagonizes the vitamin D receptor. In another aspect, methods of treating hypercalcemia, hyperparathyroidism, sarcoidosis, or vitamin D intoxication are provided. The methods include administering an effective amount of a compound of the present technology or a pharmaceutical composition comprising an effective amount of a compound of the present technology to a subject suffering from hypercalcemia, hyperparathyroidism, sarcoidosis, or vitamin D intoxication.

Compounds of formula IV, IVA, IVB, VA, VB, VIA, VIB, VIC, VID, VIIA, VIIB, VIIIA, VIIIB, VIIIC, and VIIID may be present in a composition to treat the above-noted diseases and disorders in an effective amount and optionally including a pharmaceutically acceptable carrier. In some embodiments, the amount of compound includes from about 0.01 μg per gram of composition to about 1 mg per gram of the composition, preferably from about 0.1 μg per gram to about 500 μg per gram of the composition, and may be administered topically, transdermally, orally, or parenterally in dosages of from about 0.01 μg per day to about 1 mg per day, preferably from about 0.1 μg per day to about 500 μg per day.

Further features and advantages of the present technology will be apparent from the following detailed description and drawings.

BRIEF DESCRIPTION OF THE DRAWINGS

FIG. 1 shows a graph of competitive binding to the nuclear vitamin D hormone receptor between PP-48 and the native hormone, $1,25(OH)_2D_3$. PP-48 binds to the nuclear vitamin D receptor with lower affinity than the native hormone.

FIG. 2 is a graph comparing the percent HL-60 cell differentiation as a function of the concentration of PP-48 with that of $1,25(OH)_2D_3$. PP-48 is ~10 times less potent than the native hormone in causing the differentiation of HL-60 cells into monocytes.

FIG. 3 is a graph comparing the in vitro transcription activity of PP-48 with that of $1,25(OH)_2D_3$. In bone cells, PP-48 is ~10 times less potent than the native hormone in increasing transcription of the 24-hydroxylase gene and shows no antagonistic activity.

FIG. 4 is a bar graph comparing the bone calcium mobilization activity of PP-48 with that of $1,25(OH)_2D_3$ in rat. PP-48 is essentially inactive in releasing bone calcium stores at the doses tested.

FIG. 5 is a bar graph comparing the intestinal calcium transport activity of PP-48 with that of $1,25(OH)_2D_3$ in rat. PP-48 shows a potency similar to that of the native hormone in promoting intestinal calcium transport.

FIG. 6 shows a graph of competitive binding to the nuclear vitamin D hormone receptor between AS-51 and $1,25(OH)_2D_3$. AS-51 competes for binding to the nuclear vitamin D receptor with similar affinity as the native hormone.

FIG. 7 is a graph comparing the percent HL-60 cell differentiation as a function of the concentration of AS-51 with that of $1,25(OH)_2D_3$. AS-51 does not effectively promote cellular differentiation, but is a potent inhibitor of the native hormone in causing the differentiation of HL-60 cells into monocytes.

FIG. 8 is a graph comparing the in vitro transcription activity of AS-51 with that of $1,25(OH)_2D_3$. In bone cells, AS-51 is ~60 times less potent than the native hormone in increasing transcription of the 24-hydroxylase gene. AS-51 inhibits gene transactivation stimulated by the native hormone.

FIG. 9 is a bar graph comparing the bone calcium mobilization activity of AS-51 with that of $1,25(OH)_2D_3$ in rat. AS-51 is essentially inactive in releasing bone calcium stores at the doses tested.

FIG. 10 is a bar graph comparing the intestinal calcium transport activity of AS-51 with that of $1,25(OH)_2D_3$ in rat.

Figure 1:
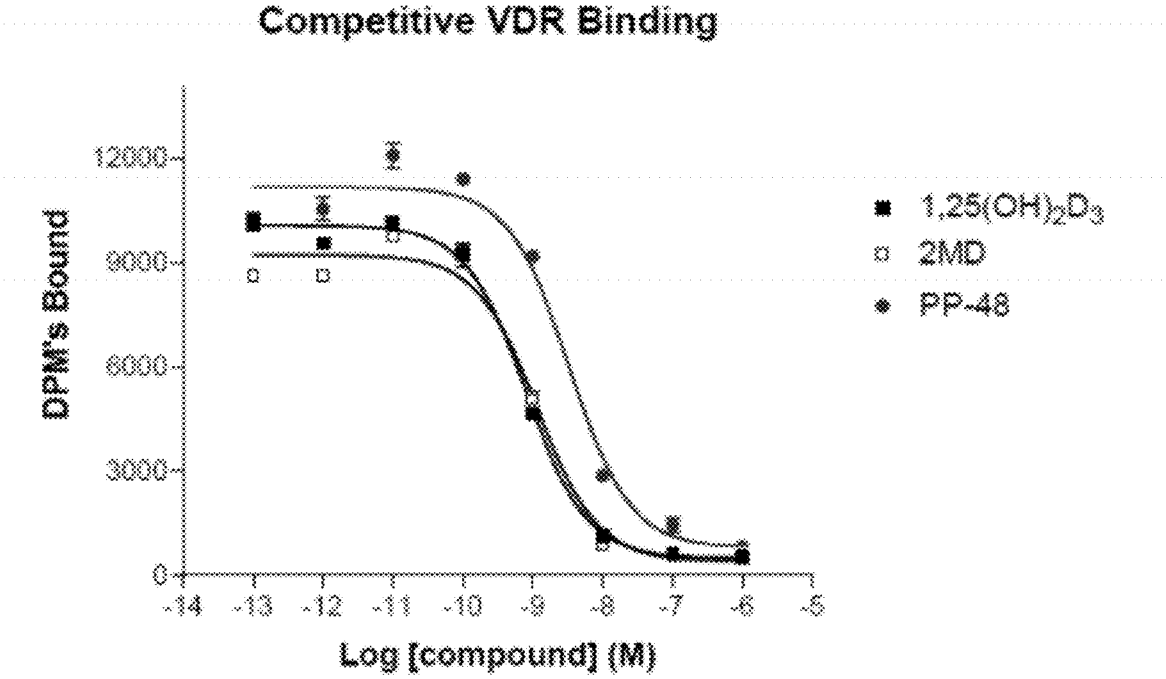
FIGS. 1-5 illustrate various biological activities of (20R,22E)-2-methylene-25-(4-methylpentanoyl)-24-oxo-26,27-cyclo-22-dehydro-1α-hydroxy-19-norvitamin $D_3$ (referred to as "PP-48" in the figures), compared with those of the native hormone, 1α,25-dihydroxyvitamin $D_3$ (referred to as "$1,25(OH)_2D_3$" in the figures).

AS-51 shows a potency less than that of the native hormone at low doses in promoting intestinal calcium transport.

DETAILED DESCRIPTION (20R,22E)-2-Methylene-25-(4-methylpentanoyl)-24-oxo-26,27-cyclo-22-dehydro-1α-hydroxy-19-norvitamin $D_3$ and (20R,22E,24R)-25-carbobutylsulfanyl-2-methylene-26,27-cyclo-22-dehydro-1α,24-dihydroxy-19-norvitamin $D_3$ were synthesized, tested, and found to be useful in treating a variety of biological conditions as described herein. Structurally, these compounds have the formulas IIIA and VIIIA as shown below.

IIIA

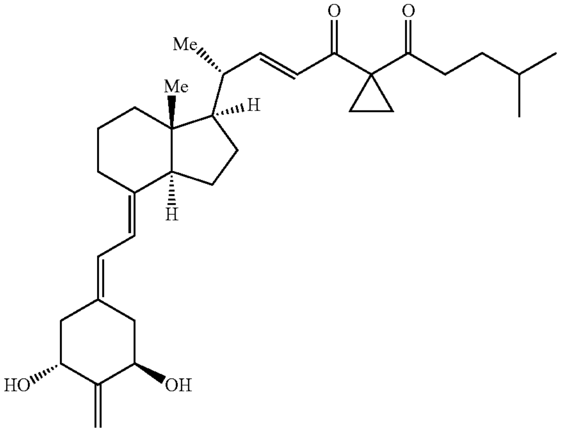

VIIIA

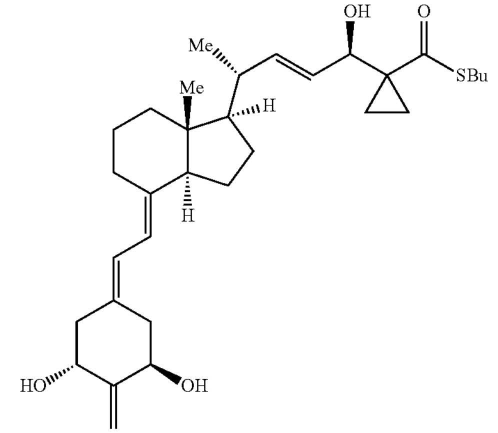

The preparation of (22E)-2-methylene-25-alkanoyl-24-oxo-26,27-cyclo-22-dehydro-1α-hydroxy-19-norvitamin $D_3$ derivatives (F) can be generally accomplished using precursors derived from vitamin $D_2$ (Scheme 1). In particular, condensing an appropriate bicyclic Windaus-Grundmann-type ketone A with the allylic phosphine oxide reagent B, provides triply-protected compound C, which possesses a 2-methylene-19-norvitamin D core. Deprotection of the acetate-protected alcohol and subsequent oxidation provides aldehyde D. The cyclopropane-containing side chain is installed via Wittig-Horner olefination with reagent E. Subsequent deprotection (i.e., removal of the $Y^1$ and $Y^2$ groups) yields the (22E)-2-methylene-25-alkanoyl-24-oxo-26,27-cyclo-22-dehydro-1α-hydroxy-19-norvitamin $D_3$ (F).

Scheme 1

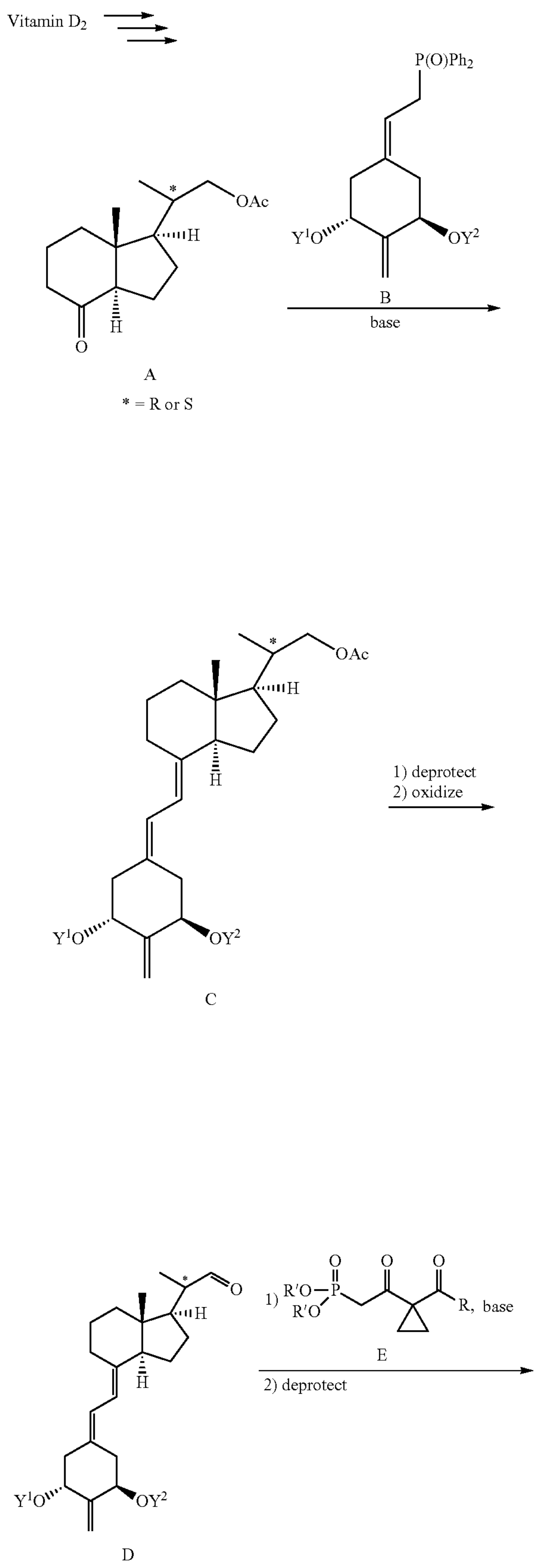

-continued

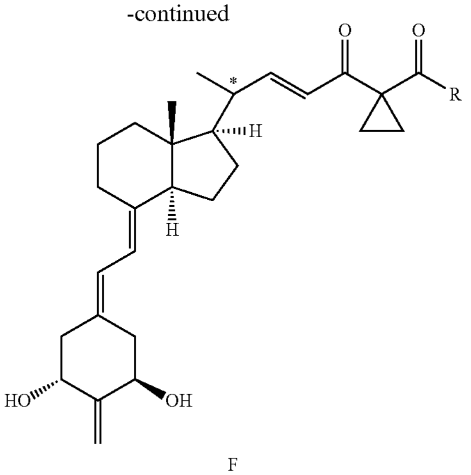

F

* = R or S

The 20R- and 20S-diastereomers of bicyclic ketone A can readily be prepared either by known methods, for example, as described in U.S. Pat. Nos. 7,915,242 and 7,713,953, each of which is hereby incorporated by reference in its entirety and for all purposes as if fully set forth herein, or by slight modification of known methods as will be readily apparent to one of skilled in the art and described herein. Details for preparing the 20R-diastereomer of bicyclic ketone A are set forth in the Examples herein. Specific examples of some important bicyclic ketones used to synthesize vitamin D analogs are those described in Mincione et al., *Synth. Commun.* 19, 723, (1989); and Peterson et al., *J. Org. Chem.* 51, 1948, (1986). An overall process for synthesizing 2-alkylidene-19-norvitamin D compounds is illustrated and described in U.S. Pat. No. 5,843,928, which is hereby incorporated by reference in its entirety and for all purposes as if fully set forth herein.

In phosphine oxide B, $Y_1$ and $Y_2$ are hydroxy protecting groups such as silyl protecting groups. The t-butyldimethylsilyl (TBDMS or TBS) group is an example of a particularly useful hydroxy protecting group. The process described above represents an application of the convergent synthesis concept, which has been applied effectively to the preparation of numerous vitamin D compounds (see Lythgoe et al., *J. Chem. Soc. Perkin Trans. I,* 590 (1978); Lythgoe, *Chem. Soc. Rev.* 9, 449 (1983); Toh et al., *J. Org. Chem.* 48, 1414 (1983); Baggiolini et al., *J. Org. Chem.* 51, 3098 (1986); Sardina et al., *J. Org. Chem.* 51, 1264 (1986); *J. Org. Chem.* 51, 1269 (1986); DeLuca et al., U.S. Pat. No. 5,086,191; DeLuca et al., U.S. Pat. No. 5,536,713; and DeLuca et al., U.S. Pat. No. 5,843,928, all of which are hereby incorporated by reference in their entirety and for all purposes as if fully set forth herein).

Phosphine oxide B is a convenient reagent that may be prepared according to the procedures described by Sicinski et al., *J. Med. Chem.,* 41, 4662 (1998), DeLuca et al., U.S. Pat. No. 5,843,928; Perlman et al., *Tetrahedron Lett.* 32, 7663 (1991); and DeLuca et al., U.S. Pat. No. 5,086,191. Scheme 2 shows the general procedure for synthesizing phosphine oxide B (where $Y^1$ and $Y^2$ are TBDMS groups) as outlined in U.S. Pat. No. 5,843,928 which is hereby incorporated by reference in its entirety as if fully set forth herein.

Scheme 2

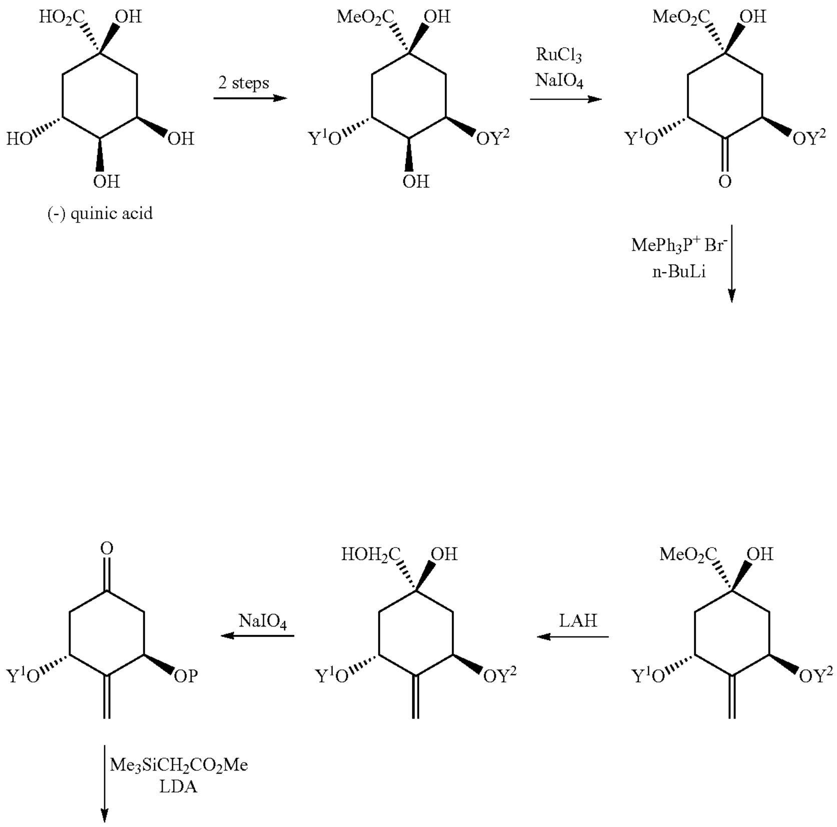

(-) quinic acid

-continued

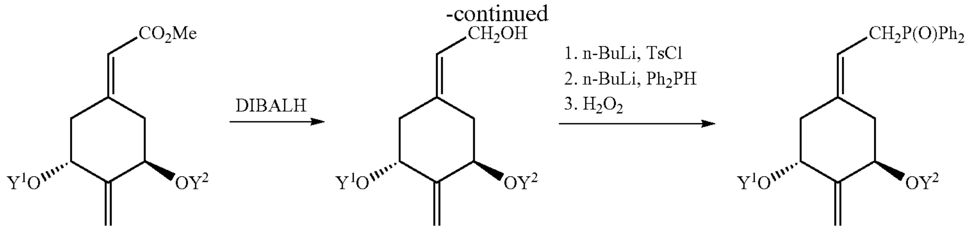

($Y^1 = Y^2$ = TBDMS)

B

Wittig-Horner reagent E from Scheme 1 may be prepared by slight modification of known methods as will be readily apparent to one of skilled in the art and described herein. Referring to Scheme 3, Claisen-type condensation of methyl acetate with a methyl ketone provides a 1,3-diketone, which, upon reaction with dibromoethane in the presence of base, yields a 1,1-disubstituted cyclopropane. Bromination of the methyl ketone followed by Arbuzov rearrangement with a trialkylphosphite provides phosphonate reagent E. By employing various methyl ketones in the Claisen condensation reaction a wide variety of phosphonate reagents may be prepared in a modular fashion.

Scheme 3

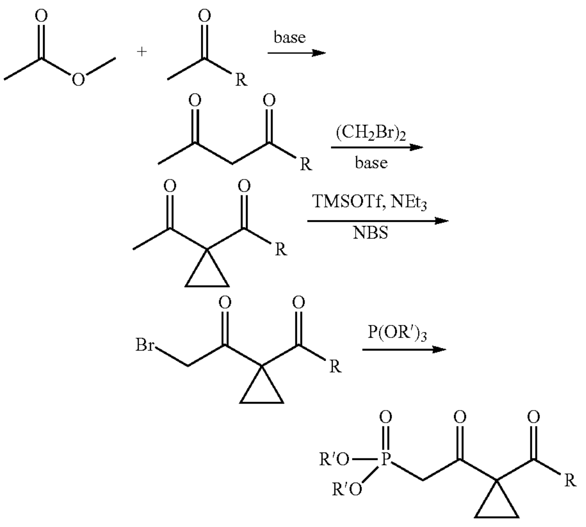

E

The preparation of (22E)-25-carboalkylsulfanyl-2-methylene-26,27-cyclo-22-dehydro-1α,24-dihydroxy-19-norvitamin $D_3$ derivatives can generally be accomplished using precursors derived from vitamin $D_2$ (Scheme 4). In particular, the reaction of protected aldehyde F with phosphonate reagent G, followed by deprotection provides compound H. The bicyclic aldehyde F can readily be prepared in diastereomerically pure form by known methods, for example, as described in U.S. Pat. Nos. 7,915,242 and 7,713,953, each of which is hereby incorporated by reference in its entirety and for all purposes as if fully set forth herein, or by slight modification of known methods as will be readily apparent to one of skilled in the art and described herein. Reduction of the enone of H with borohydride followed by selective protection of the allylic alcohol and further oxidation of the ring hydroxyl group provides Grundmann type ketone I. Depending upon the reducing reagent conditions employed, the reduction of the enone of H may occur with varying levels of diastereocontrol, thus providing access to both the 24R and the 24S epimers (readily separable). Reaction of I with phosphine oxide B and subsequent global deprotection provides (22E)-25-carboalkylsulfanyl-2-methylene-26,27-cyclo-22-dehydro-1α,24-dihydroxy-19-norvitamin $D_3$ derivatives J.

Scheme 4

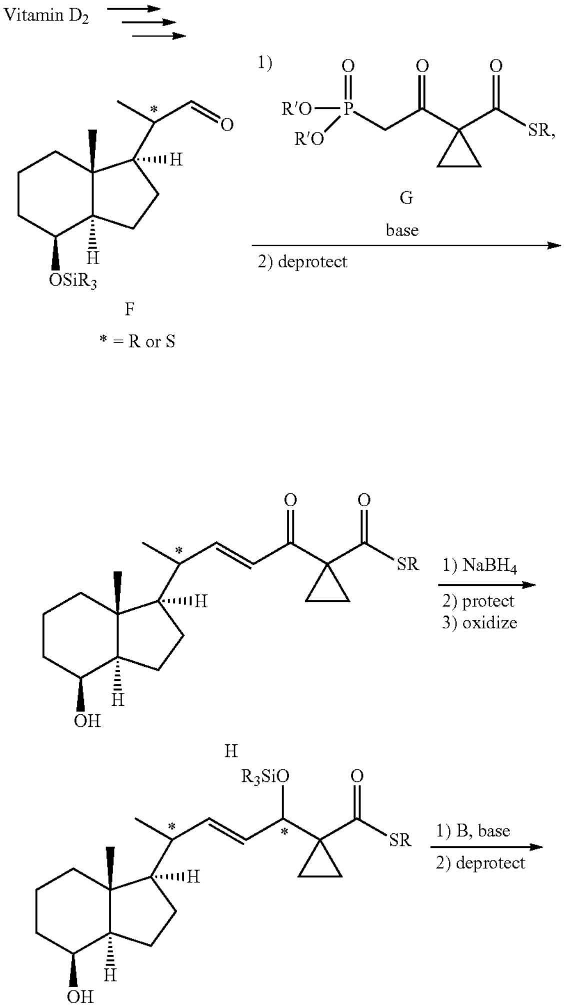

I

-continued

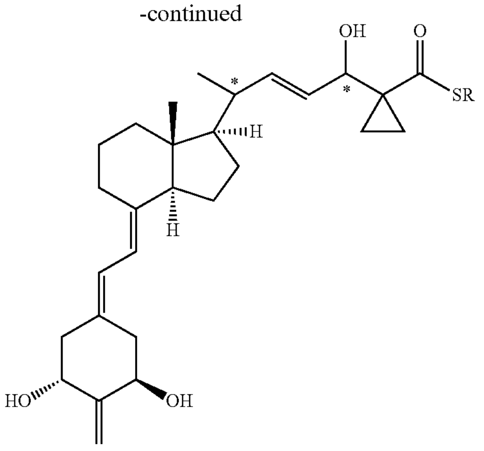

J

* = R or S

The preparation of (22E)-25-carboalkylsulfanyl-2-methylene-24-oxo-26,27-cyclo-22-dehydro-1α-hydroxy-19-nor-vitamin $D_3$ derivatives K may be accomplished by a number of

K

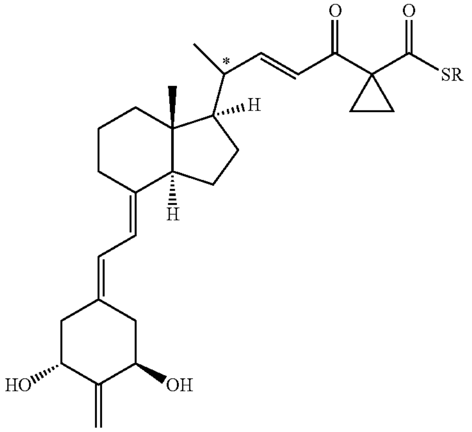

* = R or S strategies, including but not limited to: (i) direct oxidation of compound H to a cyclohexanone, followed by reaction with phosphine oxide B in the presence of base and subsequent deprotection or (ii) the reaction of phosphonate G with aldehyde D from Scheme I followed by deprotection as similarly set forth in U.S. Pat. No. 7,915,242.

Phosphonate reagent G may be prepared by slight modification of known methods as will be readily apparent to one of skilled in the art and described herein. As shown in Scheme 5, reaction of methyl acetoacetate with dibromoethane in the presence of base yields methyl 1-acetylcyclopropanecarboxylate. Hydrolysis of the ester group, activation of the carboxylic acid as an N-hydroxysuccinimide ester, and subsequent displacement with alkanethiol provides the S-alkyl 1-acetylcyclopropanecarbothioate. α-Bromination of the methyl ketone followed by Arbuzov rearrangement with a trialkylphosphite provides phosphonate reagent G. By employing various alkanethiols in the transesterification reaction, a wide variety of reagents may be prepared in a modular fashion.

Scheme 5

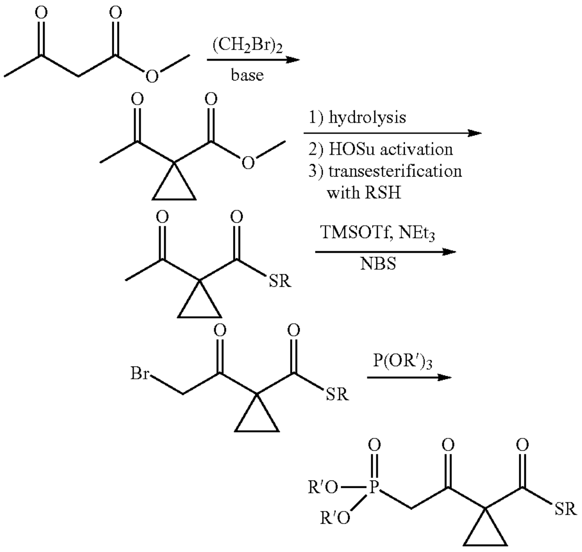

G

As used herein, the term “hydroxy protecting group” signifies any group commonly used for the temporary protection of the hydroxy (—OH) functional group, such as, but not limited to, alkoxycarbonyl, acyl, alkylsilyl or alkylarylsilyl groups (hereinafter referred to simply as “silyl” groups), and alkoxyalkyl groups. Alkoxycarbonyl protecting groups are alkyl-O—CO— groups such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term “acyl” signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. Alkoxyalkyl protecting groups are groups such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term “aryl” specifies a phenyl-, or an alkyl-, nitro- or halo-substituted phenyl group. An extensive list of protecting groups for the hydroxy functionality may be found in Protective Groups in Organic Synthesis, Greene, T. W.; Wuts, P. G. M., John Wiley & Sons, New York, N.Y., (3rd Edition, 1999), which can be added or removed using the procedures set forth therein, and which is hereby incorporated by reference in its entirety and for all purposes as if fully set forth herein.

A “protected hydroxy” group is a hydroxy group derivatized or protected by any of the above groups commonly used for the temporary or permanent protection of hydroxy functional groups, e.g., the silyl, alkoxyalkyl, acyl or alkoxycarbonyl groups, as previously defined.

Figure 2:
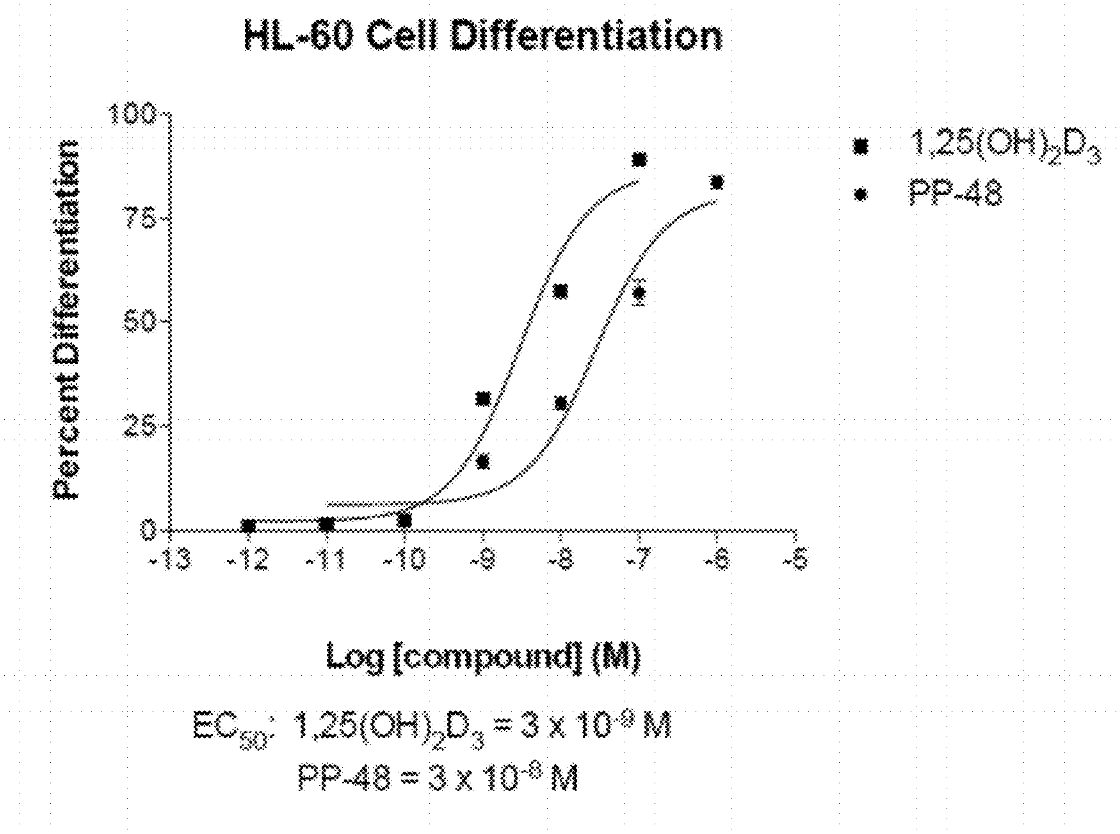
Figure 3:
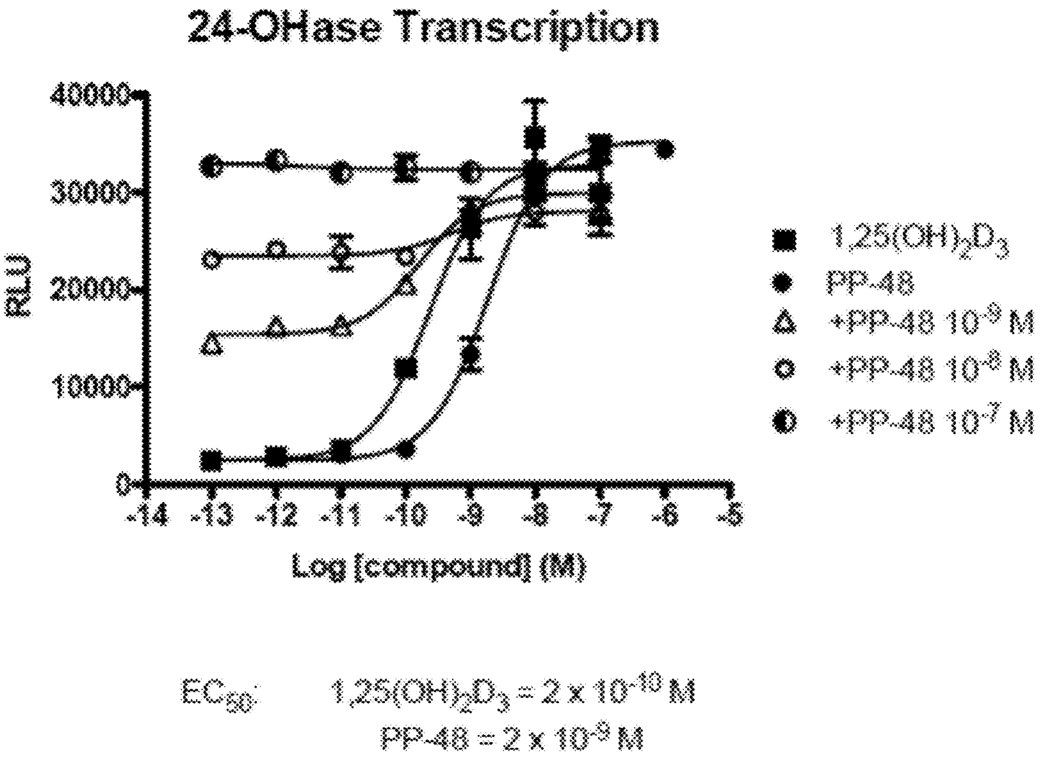
Figure 4:
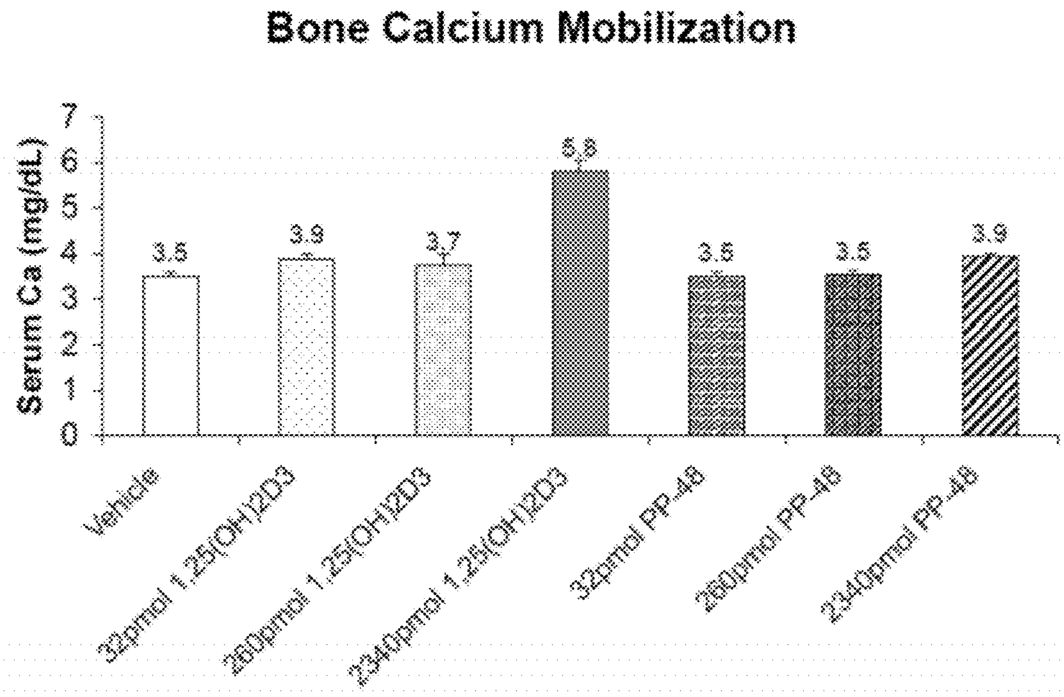
Figure 5:
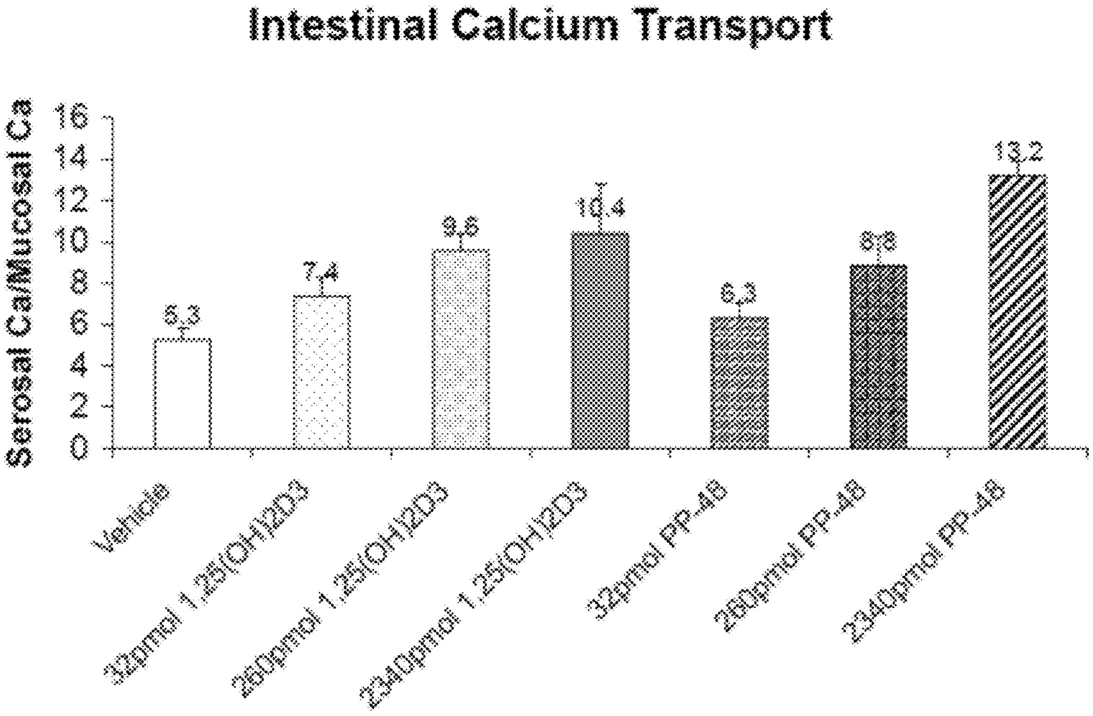
Figure 6:
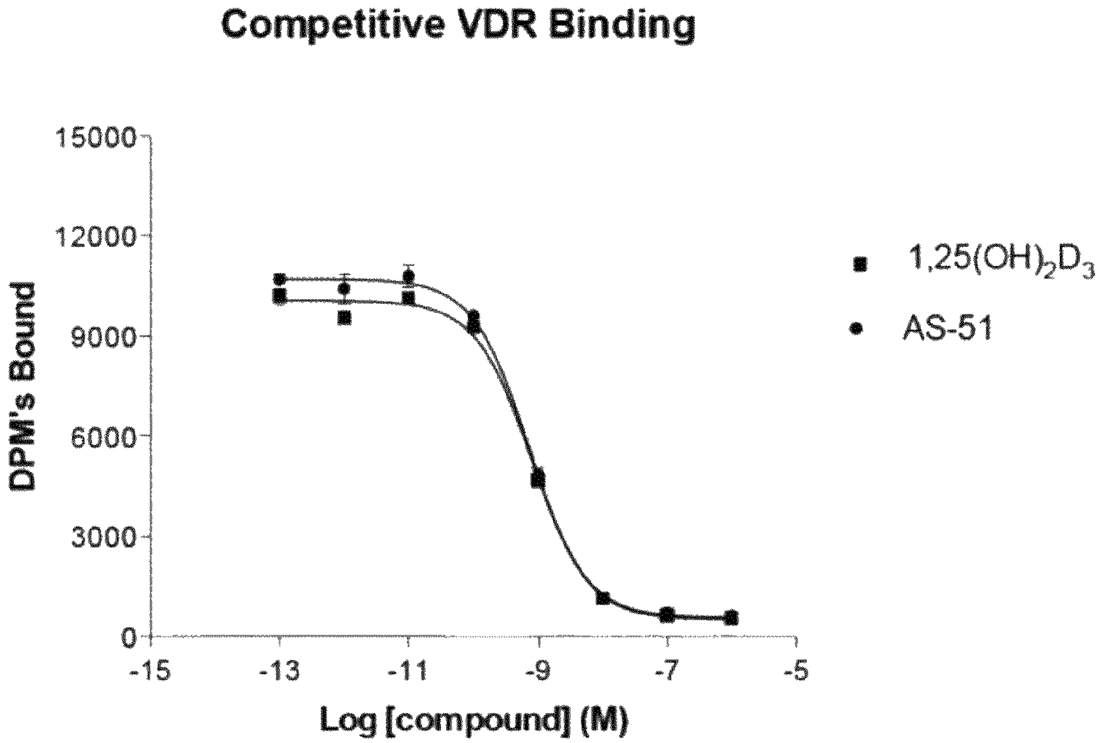
FIGS. 6-10 illustrate various biological activities of (20R,22E,24R)-25-carbobutylsulfanyl-2-methylene-26,27-cyclo-22-dehydro-1α,24-dihydroxy-19-norvitamin $D_3$ (referred to as "AS-51" in the figures), compared with those of the native hormone.
Figure 9:
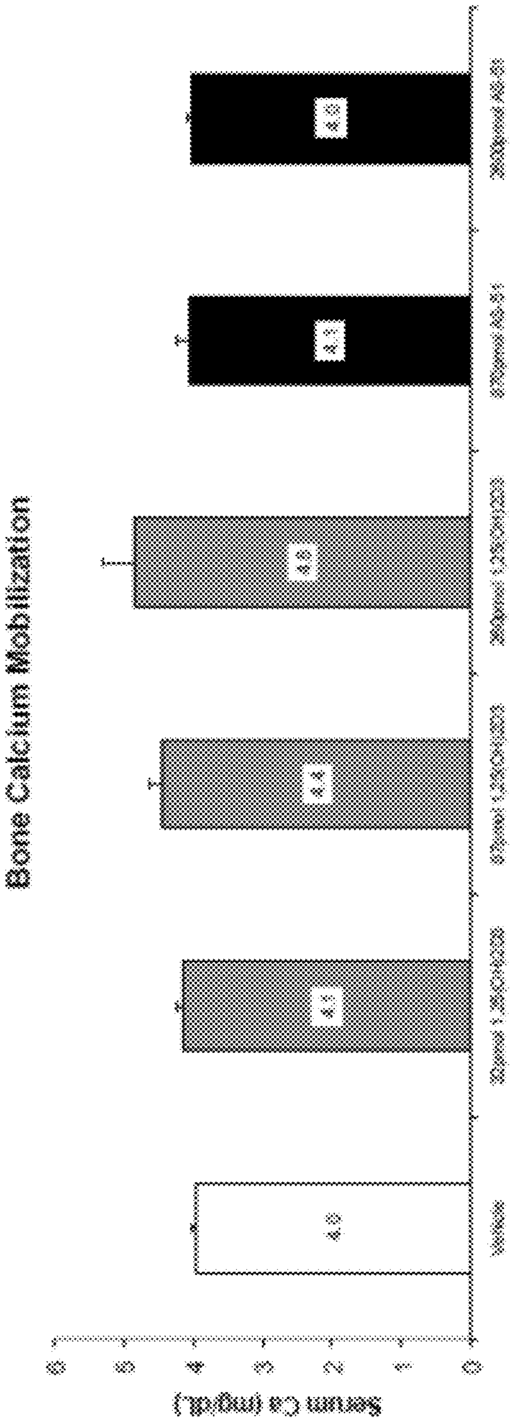
Figure 10:
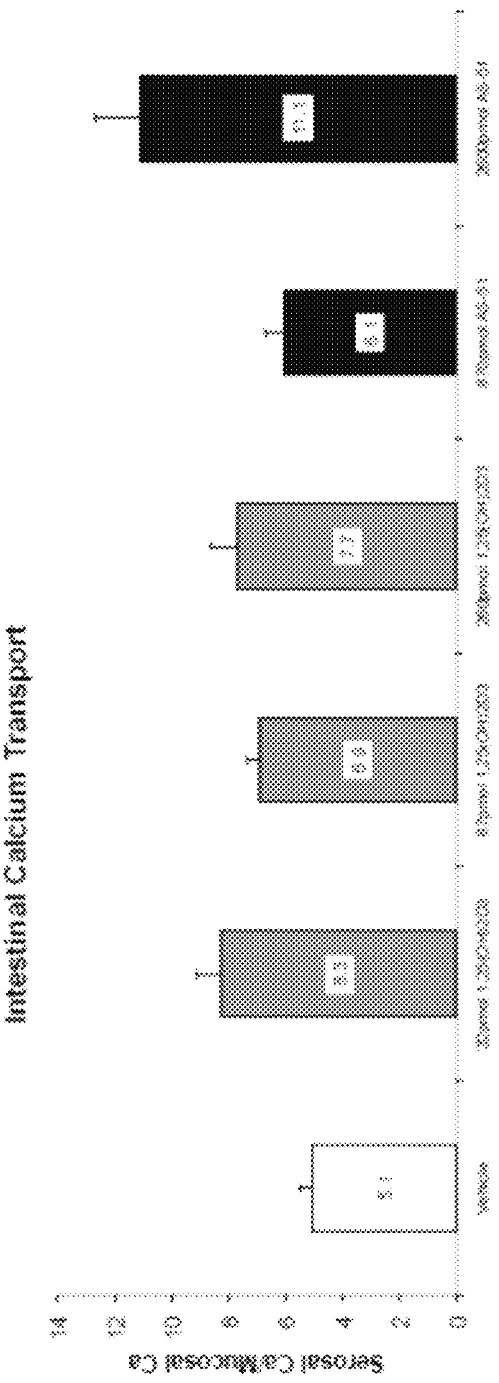

The compounds of the present technology show significant biological activity. Both PP-48 and AS-51 bind the vitamin D receptor (FIG. 1 and FIG. 6). PP-48 is active in causing HL-60 differentiation in cell culture and exhibits activity in 24-hydroxylase transcription, albeit reduced from the native hormone (FIG. 2 and FIG. 3). On the other hand, AS-51 does not effectively promote cellular differentiation, but is a potent inhibitor of the native hormone in causing the differentiation of HL-60 cells into monocytes. In the case of 24-hydroxylase activity, AS-51 is ~60 times less potent than the native hormone in causing gene transactivation, and further inhibits gene transactivation stimulated by the native hormone. In vivo studies indicated that neither PP-48 nor AS-51 demonstrate any appreciable ability to mobilize calcium from bone (FIG. 4 and FIG. 9). While both PP-48 and AS-51 increased intestinal calcium transport activity at very high doses in vivo (e.g., 2340-2600 pmol), only PP-48 increased such transport significantly at moderate doses (cf. FIG. 5 and FIG. 10).

In view of the biological activity of PP-48, compounds of formulas II, IIA, IIB, IIIA, and IIIB of the present technology may be used for treatment and prophylaxis of human disorders which are characterized by an imbalance in the immune system, e.g., in autoimmune diseases, including multiple sclerosis, lupus, diabetes mellitus, host versus graft reaction, and rejection of organ transplants; and additionally for the treatment of inflammatory diseases, such as rheumatoid arthritis, asthma, and inflammatory bowel diseases such as celiac disease, ulcerative colitis and Crohn's disease. Further, PP-48 and compounds of formula II, formula IIA, and formula IIB should find utility in the treatment of secondary hyperparathyroidism of patients suffering from chronic kidney failure because it is undesirable to elevate serum calcium above normal in these patients for fear of calcification of heart, aorta and other vital organs while suppressing parathyroid gland proliferation and transcription of the preproparathyroid gene.

In view of the relatively high cell differentiation activity of PP-48, compounds of formulas II, IIA, IIB, IIIA, and IIIB may also be used in the treatment of psoriasis, or as anti-cancer agents, especially against leukemia, colon cancer, breast cancer and prostate cancer. In addition, due to their relatively high cell differentiation activity, these compounds provide a therapeutic agent for the treatment of various skin conditions including wrinkles, lack of adequate dermal hydration, i.e., dry skin, lack of adequate skin firmness, i.e., slack skin, and insufficient sebum secretion. Use of these compounds thus not only results in moisturizing of skin but also improves the barrier function of skin.

In other embodiments, methods of preventing or treating obesity, inhibiting adipocyte differentiation, inhibiting SCD-1 gene transcription, and/or reducing body fat, are provided. The methods include administering an effective amount of a compound of, e.g., formulas II, IIA, IIB, IIIA, or IIIB or a pharmaceutical composition comprising an effective amount of such a compound to a subject in need thereof.

In view of the biological activity of AS-51 as an antagonist of the vitamin D receptor, compounds of formula IV, IVA, VA, VB, VIA, VIB, VIC, VID, VIIA, VIIB, VIIIA, VIIIB, VIIIC, and VIIID of the present technology may be used for treatment and prophylaxis of disorders characterized by the presence of an excess of $1,25(OH)_2D_3$. In this regard, such compounds may be useful in treating hypercalcemia, hyperparathyroidism, sarcoidosis, or vitamin D intoxication. Such compounds may also be used for treating conditions such as asthma or eczema.

Any of the compounds of the present technology may be used to prepare pharmaceutical formulations or medicaments that include a compound of the present technology in combination with a pharmaceutically acceptable carrier. Such pharmaceutical formulations and medicaments may be used to treat various biological disorders such as those described herein. Methods for treating such disorders typically include administering an effective amount of the compound or an appropriate amount of a pharmaceutical formulation or a medicament that includes the compound to a subject suffering from the biological disorder. The subject can be any animal that may benefit from the present compounds. In some embodiments, the subject is a mammal or a bird. In some embodiments, the mammal is selected from a rodent, a primate, a bovine, an equine, a canine, a feline, an ursine, a porcine, a rabbit, or a guinea pig. In some such embodiments, the mammal is a rat or is a mouse. In some embodiments, the subject is a primate such as a human.

For treatment purposes, any of the present compounds may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically acceptable and non-toxic excipients such as stabilizers, antioxidants, binders, coloring agents or emulsifying or taste-modifying agents. Pharmaceutically acceptable excipients and carriers are generally known to those skilled in the art and are thus included in the present technology. Such excipients and carriers are described, for example, in "Remingtons Pharmaceutical Sciences," Mack Pub. Co., New Jersey (1991), which is hereby incorporated by reference in its entirety and for all purposes as if fully set forth herein.

The compounds may be administered orally, nasally, rectally, topically, parenterally, or transdermally. The compounds are advantageously administered by injection or by intravenous infusion or suitable sterile solutions, or in the form of liquid or solid doses via the alimentary canal, or in the form of creams, ointments, patches, or similar vehicles suitable for transdermal applications. In some embodiments, doses of from 0.001 μg to about 1 mg per day of the compound are appropriate for treatment purposes. In some such embodiments, an appropriate and effective dose may range from 0.01 μg to 1 mg per day of the compound. In other such embodiments, an appropriate and effective dose may range from 0.1 μg to 500 μg per day of the compound. Such doses will be adjusted according to the type of disease or condition to be treated, the severity of the disease or condition, and the response of the subject as is well understood in the art. The compound may be suitably administered alone, or together with another active vitamin D compound.

In some embodiments, compositions of the present technology include an effective amount of a compound of formula I, IA, IB, II, IIA, IIB, IIIA, IIIB, IV, IVA, IVB, VA, VB, VIA, VIB, VIC, VID, VIIA, VIIB, VIIIA, VIIIB, VIIIC, or VIIID as the active ingredient, and a suitable carrier. An effective amount of the compound for use in accordance with some embodiments of the present technology will generally be a dosage amount such as those described herein, and may be administered orally, topically, transdermally, nasally, rectally, or parenterally.

Dosages as described above are suitable, it being understood that the amounts given are to be adjusted in accordance with the severity of the disease, and the condition and response of the subject as is well understood in the art.

The compound may be formulated as creams, lotions, ointments, aerosols, suppositories, topical patches, pills, capsules or tablets, or in liquid form as solutions, emulsions, dispersions, or suspensions in pharmaceutically innocuous and acceptable solvent or oils, and such preparations may contain, in addition, other pharmaceutically innocuous or beneficial components, such as stabilizers, antioxidants, emulsifiers, coloring agents, binders or taste-modifying agents.

The formulations of the present technology comprise an active ingredient in association with a pharmaceutically acceptable carrier and, optionally, other therapeutic ingredients. The carrier must be "acceptable" in the sense of being compatible with the other ingredients of the formulations and not deleterious to the recipient thereof.

Formulations of the present technology suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100 microns.

The formulations may conveniently be presented in dosage unit form and may be prepared by any of the methods well known in the art of pharmacy. The term "dosage unit" means a unitary, i.e., a single dose which is capable of being administered to a patient as a physically and chemically stable unit dose comprising either the active ingredient as such or a mixture of it with solid or liquid pharmaceutical diluents or carriers.

All references cited herein are specifically incorporated by reference in their entirety and for all purposes as if fully set forth herein.

The present technology is further illustrated by the following examples, which should not be construed as limiting in any way.

EXAMPLES

Example 1: Synthesis of (20R,22E)-2-methylene-25-(4-methylpentanoyl)-24-oxo-26,27-cyclo-22-dehydro-1α-hydroxy-19-norvitamin $D_3$ Compounds of formula I, formula IA, formula II, formula IIA, formula III, and formula IIIA were prepared using the methods shown in Scheme 6. Compounds of formula IB, formula IIB, and formula IIIB may be prepared using analogous procedures, employing the 20R diastereomer of 1. As shown in Scheme 6, compound 1 was obtained by ozonolysis of vitamin $D_2$ as described by Sicinski et al. (*J. Med. Chem.* 41, 4662-4672, 1998), followed by reduction with borohydride. Treatment of the dialcohol 1 with acetic anhydride in the presence of DMAP and triethylamine provided acetate ester 2. Compound 2 was oxidized with PDC to provide ketone 3. Wittig-Horner condensation of ketone 3 with phosphine oxide 4 in the presence of phenyllithium provided acetate-protected 5. The ring-A phosphine oxide compound 4 was synthesized as shown in Scheme 2 and as previously described. Methanolysis of compound 5 gave alcohol 6 which was oxidized under Swern-type conditions to provide aldehyde 7. Olefination with phosphonate reagent 8 provided protected enone 9. Deprotection of the silyl ethers with CSA provided compound 10 (PP-48).

Scheme 6

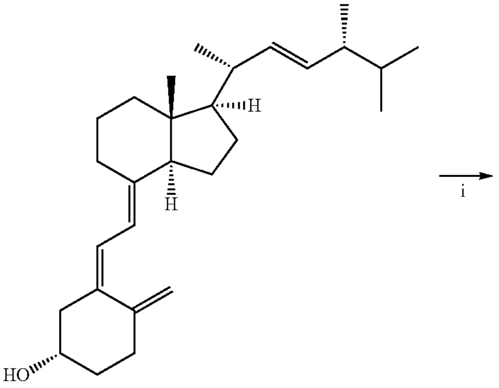

Vitamin $D_2$

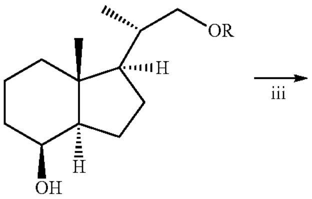

ii
1. R = H
2. R = Ac

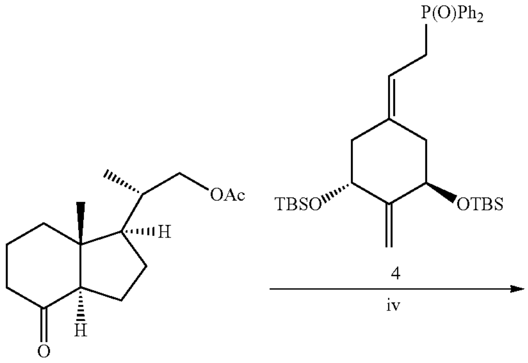

3

-continued

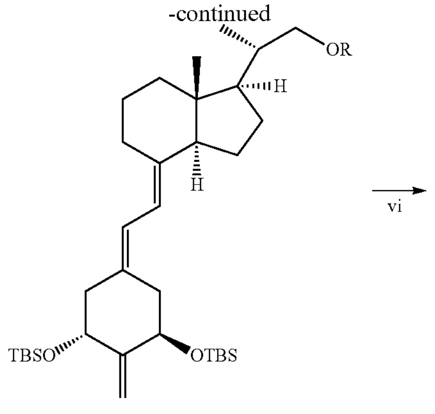

v 5. R = Ac
6. R = H

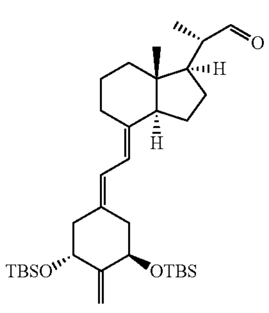

7

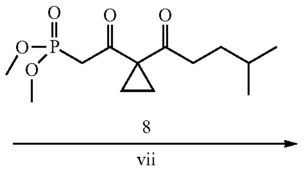

8

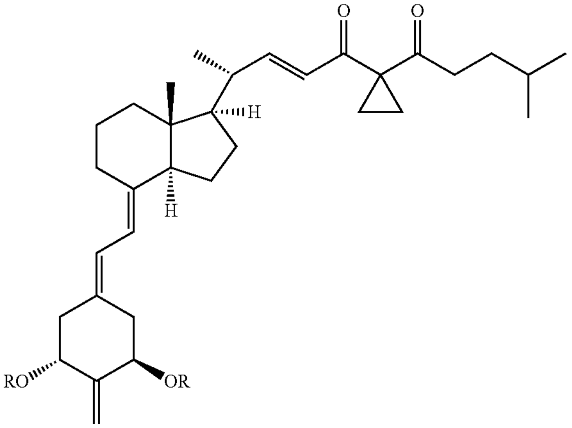

viii 9. R = TBS
10. R = H (PP-48)

(i) $O_3$, MeOH, py, $NaBH_4$, 76%; (ii) $Ac_2O$, $Et_3N$, DMAP, $CH_2Cl_2$, 98%; (iii) PDC, PPTS, $CH_2Cl_2$, 87%; (iv) 4, PhLi, THF, 44%; (v) NaOMe, MeOH, 98%; (vi) DMSO, $(COCl)_2$, $Et_3N$, $CH_2Cl_2$, 78%; (vii) 8, LiHMDS, THF; (viii) CSA, EtOH, 47% from 7.

Phosphonate reagent 8 was prepared as shown in Scheme 7. Reaction of methyl acetate (11) with 5-methylhexan-2-one (12) in the presence of sodium hydride in ether provided 7-methyloctane-2,4-dione (13). Treatment of dione 13 with dibromoethane in the presence of base provided cyclopropane 14. Bromination of cyclopropane 14 gave α-bromo compound 15. Arbuzov rearrangement with trimethylphosphite provided phosphonate reagent 8.

Scheme 7

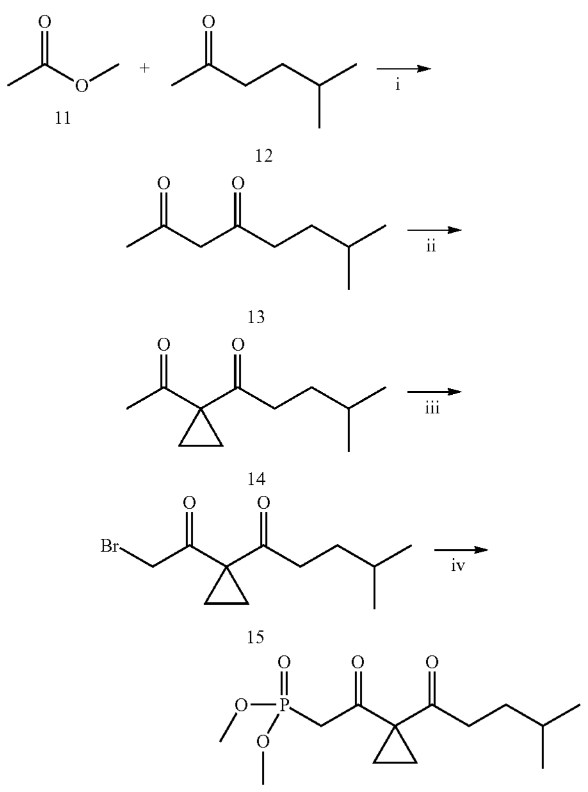

11 12 13 14 15 8

(i) 11, 12, NaH, $Et_2O$, 71%; (ii) $(CH_2Br)_2$, $K_2CO_3$, TBAB, MeCN, 41%; (iii) TMSOTf, $Et_3N$, $CH_2Cl_2$, NBS, 28%; (iv) $P(OMe)_3$, PhMe, 68%.

(20S)-Des-A,B-23,24-dinorcholane-8β,22-diol (1)

A solution of vitamin $D_2$ (5.00 g; 12.7 mmol) in methanol (400 ml) and pyridine (5 ml) was cooled to −78° C. while purging with argon. The argon stream was stopped and a stream of ozone was passed until blue color appeared. The solution was purged with oxygen until blue color disappeared and treated with sodium borohydride (1.20 g; 31.7 mmol). After 20 minutes, the second portion of sodium borohydride (1.20 g; 31.7 mmol) was added and reaction was allowed to warm to room temperature. The third portion of sodium borohydride (1.20 g; 31.7 mmol) was added and reaction mixture was stirred at room temperature overnight. The reaction was quenched with water (70 ml) and concentrated under vacuum. The residue was extracted with methylene chloride (3×100 ml). The organic phase was washed with 1M aqueous solution of HCl (2×100 ml), saturated aqueous solution of $NaHCO_3$ (100 ml), dried over anhydrous $MgSO_4$ and concentrated under vacuum. The residue was purified by flash chromatography (25% ethyl acetate/hexane) to yield 2.05 g (9.69 mmol; 76% yield) of diol 1 as white crystals. $[\alpha]_D$=+56.0 (c 0.95, $CHCl_3$); mp 110-111° C.; $^1H$ NMR (400 MHz, $CDCl_3$) δ 0.96 (3H, s), 1.03 (3H, d, J=6.6 Hz), 3.38 (1H, dd, J=10.5 Hz, J=6.8 Hz), 3.64 (1H, dd, J=10.5 Hz, J=3.2 Hz), 4.09 (1H, d, J=2.3 Hz); $^{13}C$ NMR (101 MHz, $CDCl_3$) δ 13.6, 16.6, 17.4, 22.6, 26.6, 33.5, 38.2, 40.2, 41.3, 52.3, 52.9, 67.8, 69.2; MS (EI) m/z 212 ($M^+$, 2), 194 (17), 179 (18), 163 (10), 135 (19), 125 (34), 111 (100); exact mass calculated for $C_{13}H_{22}O$ ($[M-H_2O]^+$) 194.1671, found 194.1665.

(20S)-Des-A,B-22-(acetoxy)-23,24-dinorcholane-8β-ol (2)

To a stirred solution of 1 (54 mg; 0.26 mmol) and triethylamine (50 μl; 36 mg; 0.36 mmol) in methylene chloride (5 ml) acetic anhydride was added dropwise at −5° C. The reaction mixture was kept at 4° C. overnight. Then methylene chloride (30 ml) was added and the mixture was washed with water (7 ml). The organic phase was dried over anhydrous $MgSO_4$ and concentrated under reduced pressure to give 65 mg (0.25 mmol; 98% yield) of 2. $[\alpha]_D$=+33.7 (c 0.90, $CHCl_3$); mp 78-80° C.; $^1H$ NMR (500 MHz, $CDCl_3$) δ 0.96 (3H, s), 1.00 (3H, d, J=6.6 Hz), 2.05 (3H, s), 3.77 (1H, dd, J=10.6 Hz, J=7.7 Hz), 4.06 (1H, dd, J=10.6 Hz, J=3.3 Hz), 4.11 (1H, br s); $^{13}C$ NMR (101 MHz, $CDCl_3$) δ 13.5, 17.0, 17.4, 21.0, 22.5, 26.6, 33.5, 35.3, 40.2, 41.9, 52.3, 53.2, 69.1, 69.4, 171.4; MS (EI) m/z 254 ($M^+$, 2), 236 (5), 205 (2), 194 (12), 176 (22), 161 (14), 135 (16), 125 (34), 111 (100); exact mass (ESI) calculated for $C_{15}H_{23}O_3Na$ ($[M+Na]^+$) 277.1780, found 277.1791.

(20S)-Des-A,B-22-(acetoxy)-23,24-dinorcholane-8-one (3)

To a stirred solution of 2 (64 mg; 0.25 mmol) and pyridiniump-toluenesulfonate (10 mg; 0.04 mmol) in methylene chloride (12 ml) pyridinium dichromate (244 mg; 0.65 mmol) was added at 0° C. The cooling bath was then removed and the reaction mixture was stirred for 2.5 hours. After that solvent was removed under reduced pressure and the residue was purified on silica gel Sep-Pack cartridge (15-25% ethyl acetate/hexane) to give 55 mg (0.22 mmol; 87% yield) of 3. $^1H$ NMR (400 MHz, $CDCl_3$) δ 0.66 (3H, s), 1.06 (3H, d, J=6.6 Hz), 2.47 (1H, dd, J=11.5 Hz, J=7.6 Hz), 3.82 (1H, dd, J=10.7 Hz, J=7.2 Hz), 4.08 (1H, dd, J=10.7 Hz, J=3.3 Hz); $^{13}C$ NMR (101 MHz, $CDCl_3$) δ 12.5, 17.2, 19.2, 21.0, 24.0, 27.0, 35.5, 38.8, 40.9, 49.9, 53.3, 61.6, 69.1, 171.3, 211.6; MS (EI) m/z 252 ($M^+$, 18) 237 (18), 220 (24), 205 (64) 192 (80), 124 (100); exact mass (ESI) calculated for $C_{15}H_{21}O_3Na$ ($[M+Na]^+$) 275.1623, found 275.1631.

(20S)-22-Acetoxy-1α-[(tert-butyldimethylsilyl)oxy]-2-methylene-19-norhomoprenacalciferol tert-butyldimethylsilyl ether (5)

To a stirred solution of 4 (55 mg; 94 μmol) in tetrahydrofuran (700 μl), a few drops of 1.7 M solution of phenyllithium in cyclohexane/ether (7/3) were added at −25° C. until deep orange color persisted. Then a stoichiometric amount (50 μl; 85 μmol) of phenyllithium solution was added. After 20 minutes, the mixture was cooled down to −78° C. and a solution of 3 (23 mg; 91 μmol) in tetrahydrofuran (300 μl) was siphoned via cannula. After 2 hours, the cooling bath was removed and the reaction mixture was stirred at 4° C. for an additional 2 hours. Then saturated aqueous solution of $NH_4Cl$ (1 ml), brine (1 ml) and water (1 ml) was added and the mixture was extracted with hexane (3×7 ml). The organic phase was dried over anhydrous $MgSO_4$ and concentrated under reduced pressure. The residue was purified on silica gel Sep-Pack cartridge (0-3% ethyl acetate/hexane) to give 25 mg (40 mmol; 44% yield) of 5. $^1H$ NMR (400 MHz, $CDCl_3$) δ 0.02 (3H, s), 0.05 (3H, s), 0.06 (3H, s), 0.08 (3H, s), 0.57 (3H, s), 0.86 (9H, s), 0.89 (9H, s), 1.03 (3H, d, J=6.6 Hz), 2.06 (3H, s), 2.18 (1H, dd, J=12.6 Hz, J=8.3 Hz), 2.32 (1H, m), 2.46 (1H, dd, J=12.8 Hz, J=4.5 Hz), 2.52 (1H, dd, J=13.3 Hz, J=5.9 Hz), 2.83 (1H, m), 3.79 (1H, dd, J=10.6 Hz, J=7.5 Hz), 4.10 (1H, dd, J=10.6 Hz, J=3.2 Hz), 4.43 (2H, m), 4.92 (1H, s), 4.97 (1H, s), 5.84 (1H, d, J=11.1 Hz), 6.21 (1H, d, J=11.1 Hz); $^{13}C$ NMR (101 MHz, $CDCl_3$) δ −5.12, −4.87, 12.1, 17.3, 18.2, 21.0, 22.3, 23.3, 2×25.8, 27.2, 28.7, 36.2, 38.5, 40.4, 45.7, 47.6, 53.1, 55.9, 69.5, 71.6, 72.5, 106.3, 116.3, 122.3, 133.0, 140.7, 152.9, 171.4; MS (EI) m/z 484 (100), 366 (25), 230 (44); exact mass calculated for $C_{36}H_{64}O_4Si_2$ ($[M+Na]^+$) 639.4241, found 639.4266.

(20S)-1α-[(tert-Butyldimethylsilyl)oxy]-22-hydroxy-2-methylene-19-norhomopregnacalciferol tert-butyldimethylsilyl ether (6)

To a stirred solution of 5 (24 mg, 39 μmol) in methanol (1 ml) 10% sodium methoxide in methanol (150 μl) was added dropwise at 0° C. The cooling bath was removed and the reaction mixture was stirred for 30 minutes. Diethyl ether (20 ml) was added and the mixture was washed with saturated aqueous solution of $NH_4Cl$ (3 ml) and water (3 ml). The organic phase was dried over anhydrous $MgSO_4$ and concentrated under reduced pressure. The residue was purified on silica gel Sep-Pack cartridge (10% ethyl acetate/hexane) to give 22 mg (38 μmol; 98% yield) of 6. $^1H$ NMR (500 MHz, $CDCl_3$) δ 0.02 (3H, s), 0.05 (3H, s), 0.06 (3H, s), 0.08 (3H, s), 0.57 (3H, s), 0.86 (9H, s), 0.89 (9H, s), 1.07 (3H, d, J=6.6 Hz), 2.01 (2H, m), 2.18 (1H, dd, J=12.3 Hz, J=8.9 Hz), 2.30 (1H, m), 2.48 (1H, dd, J=12.6 Hz, J=4.3 Hz), 2.56 (1H, dd, J=13.1 Hz, J=5.6 Hz), 2.84 (1H, m), 3.41 (1H, m), 3.68 (1H, m), 4.42 (2H, m), 4.93 (1H, s), 4.98 (1H, s), 5.85 (1H, d, J=11.2 Hz), 6.25 (1H, d, J=11.2 Hz); $^{13}C$ NMR (126 MHz, $CDCl_3$) δ −5.1, −4.9, 12.1, 16.9, 22.3, 23.4, 2×25.8, 27.2, 28.7, 38.6, 39.1, 40.4, 45.7, 47.6, 52.8, 56.0, 68.0, 71.6, 72.5, 106.3, 116.2, 122.3, 140.9, 152.9. MS (EI) m/z 442 (100), 366 (28).

(20S)-1α-[(tert-Butyldimethylsilyl)oxy]-2-methylene-22-oxo-19-norhomopregnacalciferol tert-butyldimethylsilyl ether (7)

To a stirred solution of oxalyl chloride (12 μl; 18 mg; 140 μmol) in methylene chloride (400 μl) a precooled solution of dimethyl sulfoxide (40 μl; 44 mg; 560 μmol) in methylene chloride (300 μl) was added dropwise via cannula at −78° C. After 30 minutes, a solution of 6 (22 mg; 38 μmol) in methylene chloride (200 μl) was added via cannula. The reaction mixture was stirred for 15 minutes and triethylamine (42 μl; 30 mg; 300 μmol) was added. After the next 15 minutes, the cooling bath was removed and the reaction mixture was warmed to room temperature. Methylene chloride (15 ml) was then added and the mixture was washed with water (3 ml). The organic phase was dried over anhydrous $MgSO_4$ and concentrated under reduced pressure. The residue was purified on silica gel Sep-Pack cartridge (1-2% ethyl acetate/hexane) to give 17 mg (30 mmol; 78% yield) of 7. $^1H$ NMR (400 MHz, $CDCl_3$) δ 0.02 (3H, s), 0.05 (3H, s), 0.06 (3H, s), 0.08 (3H, s), 0.59 (3H, s), 0.86 (9H, s), 0.90 (9H, s), 1.14 (3H, d, J=6.8 Hz), 2.18 (1H, dd, J=12.5 Hz, J=8.4 Hz), 2.85 (1H, m), 4.43 (2H, m), 4.92 (1H, s), 4.97 (1H, s), 5.86 (1H, d, J=11.2 Hz), 6.21 (1H, d, J=11.2 Hz), 9.59 (1H, d, J=3.3 Hz); $^{13}C$ NMR (101 MHz, $CDCl_3$) δ −4.8, −4.5, 13.6, 22.5, 23.3, 2×25.8, 26.5, 38.6, 40.3, 47.6, 49.8, 51.4, 55.5, 71.6, 72.5, 106.4, 116.6, 122.2, 133.4, 140.1, 152.9, 205.0.

(20R,22E)-2-Methylene-25-(4-methylpentanoyl)-24-oxo-26,27-cyclo-22-dehydro-1-hydroxy-19-norvitamin $D_3$ (10, PP-48)

To a stirred solution of 8 (10 mg; 34 μmol) in tetrahydrofuran (150 μl), a 1M solution of lithium hexamethyldisilazide in tetrahydrofuran (30 μl; 30 μmol) was added dropwise. After 1 hour, a solution of 7 (3 mg; 5 μmol) in tetrahydrofuran (100 μl) was added via cannula and the reaction mixture was stirred for 2 days. Then diethyl ether (10 ml) was added and the mixture was washed with saturated aqueous solution of $NH_4Cl$ (1 ml) and water (1 ml). The organic phase was dried over anhydrous $MgSO_4$ and concentrated under reduced pressure. The residue was purified on silica gel Sep-Pack cartridge (1-3% ethyl acetate/hexane) 4 mg of crude 9.

To a stirred solution of 9 (4 mg; 16 μmol) in ethanol (400 μl), (1S)-(+)-10-camphorsulfonic acid (3 mg; 13 μmol) was added. After 30 hours, ethyl acetate (10 ml), saturated aqueous solution of $NaHCO_3$ (1 ml) and water (1 ml) was added. The mixture was extracted with ethyl acetate (3×10 mL). The organic phase was dried over anhydrous $MgSO_4$ and concentrated under reduced pressure. The residue was purified on silica gel Sep-Pack (10-40% ethyl acetate/hexane) and HPLC (10% 2-propanol/hexane; 4 ml/min.; Zorbax Rx-Sil 9.4 mm×25 cm; $R_t$=7.69 min.) to give 1.25 mg (2.5 μmol; 47% yield based on 7) of 10 (PP-48). UV (EtOH) $\lambda_{max}$=244, 251.5 nm; $\epsilon_{max}$=47000; $^1$H NMR (500 MHz, $CDCl_3$) δ 0.58 (3H, s), 0.87 (6H, d, J=6.2 Hz), 1.10 (3H, d, J=6.6 Hz), 1.97-2.05 (2H, m), 2.27-2.35 (3H, m), 2.55-2.59 (3H, m), 2.81-2.86 (2H, m), 4.44-4.49 (2H, m), 5.10 (1H, s), 5.11 (1H, s), 5.92 (1H, d, J=11.2 Hz), 6.14 (1H, d, J=15.7 Hz), 6.35 (1H, d, J=11.2 Hz), 6.78 (1H, dd, J=15.7 Hz, J=9.0 Hz); MS (EI) m/z 429 (14), 355 (15), 178 (39), 149 (81), 70 (100); exact mass (ESI) calculated for $C_{33}H_{48}O_4Na$ ($[M+Na]^+$) 531.3450, found 531.3447.

7-Methyl-2,4-octanedione (13)

To a stirred solution of methyl acetate 11 (27.8 ml; 25.9 g; 350 mmol) in diethyl ether (200 ml) sodium hydride (60% w/w; 4.8 g; 200 mmol) was added and the resultant slurry was brought to reflux. Then a solution of 5-methyl-2-hexanone 12 (24.6 ml; 20.0 g; 175 mmol) in diethyl ether (150 ml) was added dropwise over 3 hours. Refluxing was maintained for next 5 hours. Then 10% aqueous solution of HCl with crushed ice (ca. 100 ml) was added carefully and the organic phase was separated. The aqueous phase was extracted with diethyl ether (150 ml) and the combined organic phases were washed with saturated aqueous solution of $NaHCO_3$ (50 ml), dried over anhydrous $MgSO_4$ and concentrated under reduced pressure. The residue was purified by distillation under reduced pressure to give 19.5 g (125 mmol; 71% yield) of 13. $^1$H NMR (400 MHz, $CDCl_3$) δ 0.88-0.92 (6H, m), 1.49 (2H, m), 1.57 (1H, m), 2.05 (2.6H, s), 2.13 (0.1H, s), 2.18 (0.2H, s), 2.24-2.29 (2H, m), 2.51 (0.3H, t, J=7.5 Hz), 3.58 (0.3H, s), 5.50 (0.6H, s); $^{13}$C NMR (100 MHz, $CDCl_3$) δ 22.3, 24.9, 27.5, 27.7, 30.9, 32.1, 34.6, 36.3, 44.7, 57.9, 99.7, 191.3, 194.7; exact mass (ESI) calculated for $C_9H_{16}O_2Na$ ($[M+Na]^+$) 179.1048, found 179.1040.

1-Acetyl-1-(4-methylpentanoyl)cyclopropane (14)

To a vigorously stirred mixture of 1,2-dibromoethane (16.2 ml; 35.3 g; 188 mmol), $K_2CO_3$ (34.5 g; 250 mmol), tetra-n-butylammonium bromide (4.03; 12.5 mmol) and acetonitrile (90 ml) 13 (19.5 g; 125 mmol) was added. The reaction mixture was stirred for 4 days. Then the solids were filtered off and the filtrate was concentrated under reduced pressure. The residue was purified by distillation under reduced pressure to give 8.85 g (51.4 mmol; 41% yield) of 14. $^1$H NMR (500 MHz, $CDCl_3$) δ 0.89 (6H, d, J=6.2 Hz), 1.43 (4H, s), 1.45-1.56 (3H, m), 2.22 (3H, s), 2.51 (2H, t, J=7.6 Hz); $^{13}$C NMR (126 MHz, $CDCl_3$) δ 16.9, 22.3, 27.6, 27.7, 32.9, 38.0, 43.0, 204.1, 206.4; MS (EI) m/z 182 ($M^+$, 24), 167 (44), 73 (100); exact mass calculated for $C_{11}H_{18}O_2$ 182.1307, found 182.1316.

1-Bromoacetyl-1-(4-methylpentanoyl)cyclopropane (15)

To a stirred solution of 14 (4.15 g; 22.8 mmol) and triethylamine (6.70 ml; 4.87 g; 48.2 mmol) in methylene chloride (250 ml) trimethylsilyl trifluoromethanesulfonate (4.65 ml; 5.35 g; 24.1 mmol) was added dropwise at 0° C. After 30 minutes, N-bromosuccinimide (4.72 g; 26.5 mmol) was added and the cooling bath was removed. Then methylene chloride (500 ml) was added and the mixture was washed with water (2×100 ml). The organic phase was dried over anhydrous $MgSO_4$ and concentrated under reduced pressure. The residue was purified by column chromatography (2-10% ethyl acetate/hexane) to give 1.65 g (6.32 mmol; 28% yield) of 15. $^1$H NMR (500 MHz, $CDCl_3$) δ 0.90 (6H, d, J=6.4 Hz), 1.50 (2H, m), 1.56 (2H, m), 1.63 (2H, m), 2.30 (2H, t, J=7.45 Hz), 4.31 (2H, s); $^{13}$C NMR (126 MHz, $CDCl_3$) δ 18.8, 22.3, 27.6, 32.7, 34.1, 35.3, 40.8, 198.5, 206.1; MS (EI) m/z 263 ($[M+H]^+$, 11), 261 ($[M+H]^+$, 12), 206 (52), 204 (51), 191 (59), 111 (96), 81 (100); exact mass (ESI) calculated for $C_{11}H_{17}O_2BrNa$ ($[M+Na]^+$) 283.0310, found 283.0299.

1-[2-(Dimethoxyphosphoryl)acetyl]-1-(4-methylpentanoyl)cyclopropane (8)

A solution of 15 (1.65 g; 6.32 mmol) and trimethyl phosphite (970 μl; 1020 mg; 8.22 mmol) in toluene (30 ml) was refluxed overnight. Then the solvent was distilled off and the residue was purified by column chromatography (5-20% isopropanol/hexane) to give 1.24 g (4.28 mmol; 68% yield) of 8. $^1$H NMR (500 MHz, $CDCl_3$) δ 0.89 (6H, t, J=6.4 Hz), 1.46-1.55 (5H, m), 1.63 (2H, m), 2.34 (2H, t, J=7.5 Hz), 3.46 (2H, d, $J_{H-P}$=22.2 Hz), 3.77 (6H, d, $J_{H-P}$=11.2 Hz); $^{13}$C NMR (126 MHz, $CDCl_3$) δ 18.7, 23.1, 28.3, 33.4, 36.7, 39.7 (d, $J_{C-P}$=129.5 Hz), 43.1, 53.6 (d, $J_{C-P}$=4.8 Hz), 198.6 (d, $J_{C-P}$=6.3 Hz), 207.1; MS (EI) m/z 291 ($[M+H]^+$, 48), 275 (35), 247 (80), 192 (87), 124 (100); exact mass (ESI) calculated for $C_{13}H_{23}O_5PNa$ ($[M+Na]^+$) 313.1181, found 313.1171.

Example 2: Synthesis of (20R,22E,24R)-25-carbobutylsulfanyl-2-methylene-26,27-cyclo-22-dehydro-1α,24-dihydroxy-19-norvitamin $D_3$ Compounds of formula IV, formula IVA, formula VIA, and formula VIIIA were prepared using the methods shown in Scheme 8. As shown in Scheme 8, treatment of the dialcohol 1 with acetic anhydride in the presence of DMAP and triethylamine provided acetate ester 2. The remaining hydroxyl group was protected with triethylsilyl triflate in methylene chloride to give compound 16. Selective deprotection with sodium methoxide in methanol provided primary alcohol 17. Oxidation of alcohol 17 provided aldehyde 18. Olefination of aldehyde 18 with phosphonate reagent 19 provided enone 20. Deprotection of the silyl ether gave alcohol 21. Luche reduction with sodium borohydride in the presence of cerium(III) chloride in ethanolic THF provided allylic alcohol 22 (along with the 24S diastereomer of 22 which was separated by column chromatography). Allylic alcohol 22 was protected as a triethylsilyl ether (compound 23). Oxidation with pyridinium dichromate gave Grundmann type ketone 24. Wittig-Horner condensation of ketone 24 with phosphine oxide 4 in the presence of phenyllithium provided tris(silyl ether) 25. Global deprotection with aqueous formic acid in THF gave compound 26 (AS-51).

Scheme 8

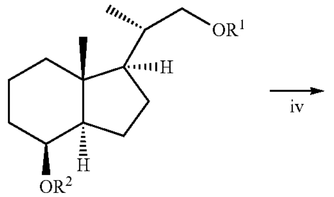

i: 1. $R^1$ = H, $R^2$ = H → 2. $R^1$ = Ac, $R^2$ = H ii: → 16. $R^1$ = Ac, $R^2$ = TES iii: → 17. $R^1$ = H, $R^2$ = TES

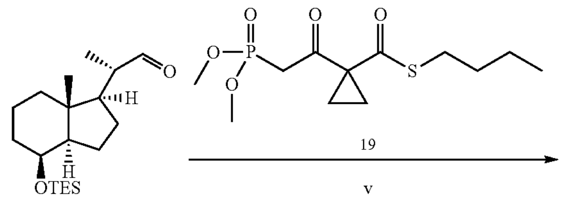

18

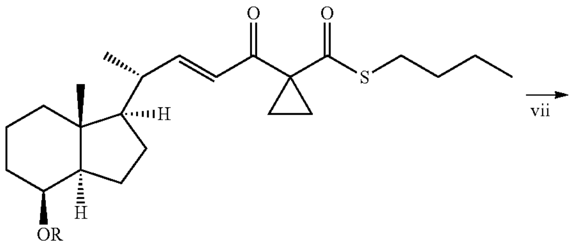

vi: 20. R = TES → 21. R = H

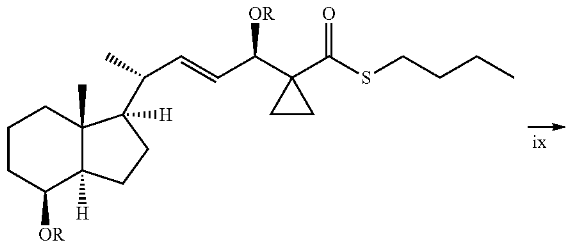

viii: 22. R = H → 23. R = TES

-continued

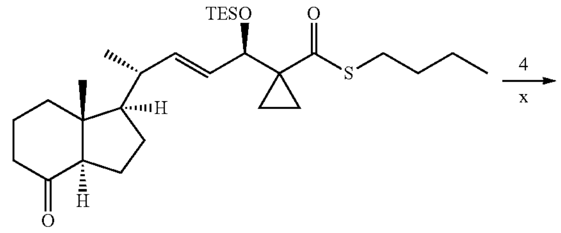

24

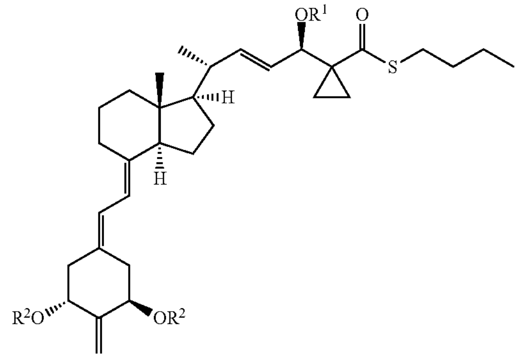

xi: 25. $R^1$ = TES, $R^2$ = TBS → 26. $R^1$ = $R^2$ = H (AS-51)

(i) $Ac_2O$, $Et_3N$, DMAP, $CH_2Cl_2$, 97%; (ii) TESOTf, 2,6-lutidine, $CH_2Cl_2$; (iii) NaOMe, MeOH, 97% from 2; (iv) $SO_3$/py, $Et_3N$, DMSO, $CH_2Cl_2$, 78%; (v) 19, LiHMDS, THF, 71%; (vi) CSA, EtOH, 92%; (vii) $NaBH_4$, $CeCl_3$•$7H_2O$, THF/EtOH, 22%; (viii) TESCl, $Et_3N$, $CH_2Cl_2$, 51%;
(ix) PDC, PPTS, $CH_2Cl_2$, 88%; (x) 4, PhLi, THF, 93%; (xi) $HCO_2H$/THF/$H_2O$, 35%.

It is noteworthy that in the course of the synthesis described in Scheme 8 that, in the preparation of 22, the 24S diastereomer of 22 was also prepared, Accordingly, the 24S diastereomer of 22 may be subjected to the same synthetic sequence as 22, thus providing access to a diastereomer of 26, i.e., (20R,22E,24S)-25-carbobutylsulfanyl-2-methylene-26,27-cyclo-22-dehydro-1α,24-dihydroxy-19-norvitamin $D_3$. Other diastereomers of 26 (e.g., (20S,22E,24S)- and (20S,22E,24R)-diastereomers) may be prepared in a similar fashion from the 20R diastereomer of 18.

Phosphonate reagent 19 was prepared as shown in Scheme 5. Reaction of methyl acetoacetate (27) with dibromoethane in the presence of base provided methyl cyclopropylcarboxylate 28. Base hydrolysis of the ester with lithium hydroxide followed by ester activation with N-hydroxysuccinimide provided an active ester which was further reacted with n-butanethiol to give thioester 29. Bromination of cyclopropane 29 gave α-bromo compound 30. Arbuzov rearrangement of the halide with trimethylphosphite provided phosphonate reagent 19.

Scheme 9

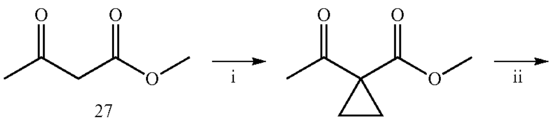

27

28

-continued

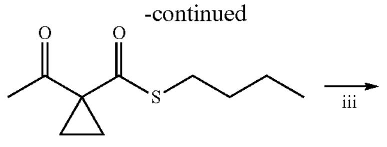

29

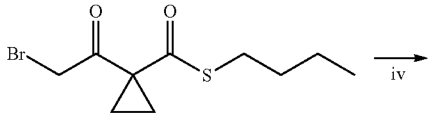

30

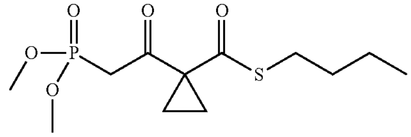

19

(i) $(CH_2Br)_2$, $K_2CO_3$, TBAB, MeCN, 67%; (ii) LiOH•$H_2O$, MeOH; 1M HCl in $Et_2O$; N-hydroxysuccinimide, DCC, DMAP, $CH_2Cl_2$; n-BuSH, $Et_3N$, $CH_2Cl_2$, 20%; (iii) TESOTf, $Et_3N$, $CH_2Cl_2$, NBS, 60%; (iv) $P(OMe)_3$, PhMe, 41%.

(20S)-Des-A,B-22-(acetoxy)-23,24-dinorcholane-8β-ol (2)

To a stirred solution of 1 (3.50 g; 16.5 mmol) and DMAP (100 mg) in triethylamine (3.00 ml; 1.67 g; 21.6 mmol) and methylene chloride (300 ml) acetic anhydride (1.54 ml; 2.18 g; 16.5 mmol) was added dropwise at 0° C. The reaction mixture was kept at 4° C. overnight. Solvents were removed under reduced pressure and the residue was redissolved in methylene chloride (200 ml), washed with 10% aqueous solution of HCl (50 ml), saturated aqueous solution of $NaHCO_3$ (50 ml) and water (50 ml). The organic phase was dried over anhydrous $Na_2SO_4$ and concentrated under reduced pressure to give 4.06 g (16.0 mmol; 97% yield) of 2 as white crystals. $[\alpha]_D$=+33.7 (c 0.90, $CHCl_3$); mp 78-80° C.; $^1H$ NMR (500 MHz, $CDCl_3$) δ 0.96 (3H, s), 1.00 (3H, d, J=6.6 Hz), 2.05 (3H, s), 3.77 (1H, dd, J=10.6 Hz, J=7.7 Hz), 4.06 (1H, dd, J=10.6 Hz, J=3.3 Hz), 4.11 (1H, br s); $^{13}C$ NMR (101 MHz, $CDCl_3$) δ 13.5, 17.0, 17.4, 21.0, 22.5, 26.6, 33.5, 35.3, 40.2, 41.9, 52.3, 53.2, 69.1, 69.4, 171.4; MS (EI) m/z 254 ($M^+$, 2), 236 (5), 205 (2), 194 (12), 176 (22), 161 (14), 135 (16), 125 (34), 111 (100); exact mass (ESI) calculated for $C_{15}H_{23}O_3Na$ ($[M+Na]^+$) 277.1780, found 277.1791.

(20S)-Des-A,B-22-(acetoxy)-8β-[(triethylsilyl)oxy]-23,24-dinorcholane (16)

To a stirred solution of 2 (4.00 g; 16.6 mmol) in methylene chloride (40 ml) and 2,6-lutidine (2.67 ml; 2.46 g; 23.0 mmol) triethylsilyl trifluoromethanesulfonate (4.52 ml; 5.28 g; 20.0 mmol) was added dropwise under argon at −50° C. After 30 minutes, wet methylene chloride (5 ml) and water (80 ml) was added. The reaction mixture was extracted with methylene chloride (3×120 ml) and the organic phase was washed with saturated aqueous solution of $CuSO_4$ (50 ml), dried over anhydrous $Na_2SO_4$ and concentrated under reduced pressure to give crude 16 as oil. $[a]_D$=+42.2 (c 1.25, $CHCl_3$); $^1H$ NMR (500 MHz, $CDCl_3$) δ 0.55 (6H, q, J=7.9 Hz), 0.93 (3H, s), 0.95 (9H, t, J=8.0 Hz), 0.98 (3H, d, J=6.6 Hz), 2.05 (3H, s), 3.77 (1H, dd, J=10.6 Hz, J=7.5 Hz), 4.04-4.07 (2H, m); $^{13}C$ NMR (126 MHz, $CDCl_3$) δ 4.9, 6.9, 13.5, 17.1, 17.6, 21.0, 23.0, 26.8, 34.6, 35.4, 40.6, 42.2, 52.8, 53.4, 69.2, 69.6, 171.4; MS (EI) m/z 368 ($M^+$, 4), 339 (30), 325 (15), 177 (89), 145 (100); exact mass calculated for $C_{21}H_{40}O_3Si$ 368.2747, found 368.2748.

(20S)-Des-A,B-8β-[(triethylsilyl)oxy]-23,24-dinorcholane-22-ol (17)

To a stirred solution of crude 16 in methanol (100 ml) a 10% solution of sodium methanolate in methanol (20 ml) was added dropwise. After 2 hours, saturated aqueous solution of $NH_4Cl$ (20 ml) and water (60 ml) were added and the mixture was extracted with methylene chloride (5×100 ml). The organic phase was dried over anhydrous $Na_2SO_4$, concentrated under reduced pressure and the residue was purified on silica gel column (10-20% ethyl acetate/hexane) to give 5.25 g (16.1 mmol; 97% yield from 2) of 17. $[\alpha]_D$=+40.3 (c 1.00, $CHCl_3$); $^1H$ NMR δ 0.55 (6H, q, J=7.9 Hz), 0.93-0.97 (12H, m), 1.02 (3H, d, J=6.6 Hz), 3.37 (1H, dd, J=10.4 Hz, J=6.8 Hz), 3.63 (1H, dd, J=10 Hz, J=3.0 Hz), 4.04 (1H, d, J=1.8 Hz); $^{13}C$ NMR (101 MHz, $CDCl_3$) δ 4.9, 6.9, 13.6, 16.6, 17.6, 23.0, 26.8, 34.6, 38.3, 40.6, 42.1, 52.8, 53.1, 68.0, 69.3; MS (EI) m/z 326 ($M^+$, 10), 311 (2), 297 (93), 283 (36), 225 (16), 193 (21), 177 (100); exact mass calculated for $C_{19}H_{38}O_2Si$ 326.2641, found 326.2639.

(20S)-Des-A,B-8β-[(triethylsilyl)oxy]-23,24-dinorcholane-22-al (18)

Sulfur trioxide pyridine complex (3.71 g; 23.3 mmol) was added to the stirred solution of 17 (1.16 g; 3.56 mmol) in triethylamine (2.73 ml; 1.97 g; 19.5 mmol), anhydrous dimethyl sulfoxide (4.00 ml) and anhydrous methylene chloride (20 ml) at 0° C. under argon. After 20 minutes, methylene chloride (80 ml) was added and reaction mixture was washed with saturated aqueous solution of $CuSO_4$ (20 ml) and water (20 ml). The organic phase was dried over anhydrous $Na_2SO_4$, concentrated under reduced pressure and residue was purified on silica gel (0.5-2% ethyl acetate/hexane) to give 900 mg (2.78 mmol; 78% yield) of 18. $[\alpha]_D$=+42.6 (c 1.15, $CHCl_3$); $^1H$ NMR (400 MHz, $CDCl_3$) δ 0.57 (6H, q, J=7.9 Hz), 0.94-0.98 (12H, m), 1.10 (3H, d, J=6.8 Hz), 2.35 (1H, m), 4.07 (1H, d, J=2.5 Hz), 9.58 (1H, d, J=3.2 Hz); $^{13}C$ NMR (101 MHz, $CDCl_3$) δ 5.0, 6.9, 13.4, 13.9, 17.6, 23.3, 26.2, 34.6, 40.6, 42.7, 49.1, 51.8, 52.5, 53.2, 69.1, 205.3; MS (EI) m/z 324 ($M^+$, 4), 311 (12), 295 (100); exact mass calculated for $C_{17}H_{31}O_2Si$ ($[M-C_2H_5]^+$) 295.2093, found 295.2086.

(20R,22E)-Des-A,B-25-carbobutylsulfanyl-24-oxo-83-[(triethylsilyl)oxy]-26,27-cyclo-22-dehydrocholestan (20)

To a stirred solution of 19 (670 mg; 2.17 mmol) in anhydrous tetrahydrofuran (5 ml) 1M lithium hexamethyldisilazide in tetrahydrofuran (2.00 ml; 2.00 mmol) was added dropwise. After 1 hour, a solution of 5 (450 mg; 1.39 mmol) in anhydrous tetrahydrofuran (3 ml) was added via cannula. The reaction mixture was stirred for 2 days. A saturated aqueous solution of $NH_4Cl$ (5 ml), brine (5 ml) and water (10 ml) were added at 0° C. The resultant mixture was extracted with methylene chloride (3×50 ml). The organic phase was dried over anhydrous $MgSO_4$, concentrated under reduced pressure and the residue was purified by column chromatography (0-5% ethyl acetate/hexane) to give 501 mg (0.99 mmol; 71% yield) of 20 and 350 mg (1.14 mmol) of unreacted 19. $[\alpha]_D$=+32.8 (c 1.05, $CHCl_3$); $^1H$ NMR (400

MHz, $CDCl_3$) δ 0.55 (6H, q, J=7.9 Hz), 0.90-0.96 (15H, m), 1.06 (3H, d, J=6.5 Hz), 1.93 (1H, m), 2.27 (1H, m), 2.92 (2H, m), 4.03 (1H, d, J=1.7 Hz), 6.27 (1H, d, J=15.5 Hz), 6.78 (1H, dd, J=15.5 Hz, J=9.0 Hz); $^{13}C$ NMR (101 MHz, $CDCl_3$) δ 4.9, 6.9, 13.6, 13.8, 17.6, 17.7, 17.8, 18.9, 21.9, 23.0, 27.3, 29.1, 31.4, 34.6, 39.6, 40.6, 42.5, 43.1, 52.9, 55.6, 65.2, 69.2, 125.4, 154.3, 194.1, 197.2; MS (EI) m/z 468 (2), 446 (8), 354 (13), 293 (28), 246 (30), 167 (97), 105 (100); exact mass (ESI) calculated for $C_{29}H_{50}O_3SSiNa$ ($[M+Na]^+$) 529.3148, found 529.3139.

(20R,22E)-Des-A,B-25-carbobutylsulfanyl-24-oxo-26,27-cyclo-22-dehydrocholestan-8β-ol (21)

To a stirred solution of 20 (500 mg; 0.99 mmol) in absolute ethanol (25 ml) (1S)-(+)-10-camphorsulfonic acid (250 mg; 1.08 mmol) was added at 0° C. and the reaction mixture stirred overnight. Saturated aqueous solution of $NaHCO_3$ (10 ml) and water (10 ml) were added and the mixture was extracted with methylene chloride (4×40 ml). The organic phase was dried over anhydrous $MgSO_4$, concentrated under reduced pressure and the residue was purified on a Waters silica gel Sep-Pack cartridge (5-20% ethyl acetate/hexane) to give 360 mg (0.92 mmol; 92% yield) of 21. $[\alpha]_D$=+42.2 (c 0.85, $CHCl_3$); $^1H$ NMR (500 MHz, $CDCl_3$) δ 0.92 (3H, t, J=7.3 Hz), 0.97 (3H, s), 1.07 (3H, d, J=6.6 Hz), 1.78-1.84 (2H, m), 1.98 (1H, m), 2.28 (1H, m), 2.92 (2H, m), 4.09 (1H, s), 6.30 (1H, d, J=15.5 Hz), 6.77 (1H, dd, J=15.5 Hz, J=9.1 Hz); $^{13}C$ NMR (126 MHz, $CDCl_3$) δ 13.6, 13.7, 17.4, 17.9, 18.9, 21.9, 22.5, 27.2, 29.0, 31.3, 33.5, 39.7, 40.2, 42.2, 43.0, 52.3, 55.3, 69.1, 125.4, 154.0, 194.2, 197.3; MS (EI) m/z 392 ($M^+$, 72), 364 (3), 335 (19), 303 (50), 285 (46), 235 (54), 189 (100); exact mass calculated for $C_{23}H_{36}O_3S$ 392.2385, found 392.2394.

(20R,22E,24R)-Des-A,B-25-carbobutylsulfanyl-26,27-cyclo-22-dehdrocholestan-8β,24-diol (22)

To a stirred solution of 21 (345 mg; 0.88 mmol) in tetrahydrofuran (3 ml) and absolute ethanol (9 ml) $CeCl_3.7H_2O$ (660 mg; 1.77 mmol) and $NaBH_4$ (102 mg; 2.68 mmol) were added at 0° C. After 20 minutes, a saturated aqueous solution of $NH_4Cl$ (5 ml) and water (5 ml) were added and the mixture was extracted with ethyl acetate (3×40 ml). The organic phase was dried over anhydrous $MgSO_4$, concentrated under reduced pressure and the residue was purified by column chromatography (2-40% ethyl acetate/hexane) to give 75 mg (0.19 mmol; 22% yield) of 22, 152 mg (0.39 mmol; 44% yield) of (20R,22E,24S)-des-A,B-25-carbobutylsulfanyl-26,27-cyclo-22-dehydrocholestan-8β,24-diol and 12 mg (0.03 mmol; 3% yield) of mixture of diastereoisomers. $[\alpha]_D$=+59.5 (c 0.85, $CHCl_3$); $^1H$ NMR (500 MHz, $CDCl_3$) δ 0.91 (3H, t, J=7.3 Hz), 0.94 (3H, s), 1.01 (3H, d, J=6.6 Hz), 1.78-1.84 (2H, m), 1.97 (1H, m), 2.06 (1H, m), 2.85 (2H, t, J=7.3 Hz), 2.94 (1H, d, J=6.3 Hz), 4.07 (1H, br d, J=1.7 Hz), 4.19 (1H, m), 5.35 (1H, dd, J=15.4 Hz, J=6.7 Hz), 5.52 (1H, dd, J=15.4 Hz, J=8.7 Hz); $^{13}C$ NMR (126 MHz, $CDCl_3$) δ 12.7, 13.6, 13.7, 15.6, 17.4, 20.1, 22.1, 22.5, 27.7, 28.3, 31.5, 33.6, 37.9, 39.5, 40.3, 41.8, 52.6, 56.0, 69.3, 125.9, 140.2, 202.6; MS (EI) m/z 394 ($M^+$, 19), 376 (40), 337 (66), 287 (68), 213 (100); exact mass (ESI) calculated for $C_{23}H_{38}O_3SNa$ ($[M+Na]^+$) 417.2439, found 417.2431.

(20R,22E,24R)-Des-A,B-25-carbobutylsulfanyl-24-[(triethylsilyl)oxy]-26,27-cyclo-22-dehydrocholestan-8β-ol (23)

To a stirred solution of 22 (41 mg; 100 μmol) and triethylamine (49 μl; 35 mg; 350 μmol) in anhydrous methylene chloride (2 ml) chlorotriethylsilane (30 μl; 27 mg; 180 μmol) was added dropwise at 0° C. The reaction mixture was stirred at room temperature overnight and purified on a Waters silica gel Sep-Pack cartridge (5-15% ethyl acetate/hexane) to give 26 mg (51 μmol; 51% yield) of 23 and 22 mg (35 μmol; 35% yield) of (22E)-des-A,B-25-carbobutoxy-8β,24-di[(triethylsilyl)oxy]-26,27-cyclo-22-dehydrocholestan. $^1H$ NMR (400 MHz, $CDCl_3$) δ 0.58 (6H, q, J=7.9 Hz), 0.88-0.95 (15H, m), 0.99 (3H, d, J=6.7 Hz), 1.79-1.83 (1H, m), 1.95-2.05 (2H, m), 2.81 (2H, t, J=7.4 Hz), 4.07 (1H, s), 5.21 (1H, dd, J=15.3 Hz, J=7.4 Hz), 5.44 (1H, dd, J=15.3 Hz, J=8.9 Hz); $^{13}C$ NMR (101 MHz, $CDCl_3$) δ 5.0, 6.9, 10.9, 13.0, 13.6, 13.7, 17.4, 22.0, 22.5, 27.5, 28.2, 31.6, 33.5, 38.7, 39.6, 40.3, 41.8, 52.6, 56.0, 69.3, 70.8, 127.9, 138.9, 200.3. MS (EI) m/z 479 (76), 451 (12), 327 (36), 237 (37), 149 (55), 135 (93), 71 (100); exact mass (ESI) calculated for $C_{29}H_{52}O_3SSiNa$ ($[M+Na]^+$) 531.3304, found 531.3302.

(20R,22E,24R)-Des-A,B-25-carbobutylsulfanyl-24-[(triethylsilyl)oxy]-26,27-cyclo-22-dehydrocholestan-8-one (24)

To a stirred solution of 23 (25 mg; 49 μmol) and pyridinium p-toluenesulfonate (3 crystals) in methylene chloride (2.5 ml) pyridinium dichromate (46 mg; 122 μmol) was added at 0° C. Then the cooling bath was removed and the reaction mixture was stirred for 3 hours. Then the solvent was removed under reduced pressure and the residue was purified on a Waters silica gel Sep-Pack cartridge (5-10% ethyl acetate/hexane) to give 22 mg (43 μmol; 88% yield) of 24. $^1H$ NMR (400 MHz, $CDCl_3$) δ 0.57 (6H, q, J=7.9 Hz), 0.64 (3H, s), 0.88-0.95 (12H, m), 1.05 (3H, d, J=6.6 Hz), 2.44 (1H, dd, J=10.8 Hz, J=7.7 Hz), 2.80 (2H, t, J=7.3), 4.79 (1H, d, J=7.4 Hz), 5.25 (1H, dd, J=15.3 Hz, J=7.4 Hz), 5.47 (1H, dd, J=15.3 Hz, J=8.9 Hz); $^{13}C$ NMR (101 MHz, $CDCl_3$) δ 5.0, 6.8, 10.1, 12.7, 13.2, 13.6, 19.1, 20.2, 22.0, 24.0, 27.6, 28.2, 31.6, 38.6, 38.8, 39.6, 40.9, 49.8, 56.1, 62.0, 70.6, 128.7, 138.0, 200.5, 211.9; MS (EI) m/z 477 (100), 449 (23), 417 (14), 387 (13), 327 (39), 237 (48); exact mass calculated for $C_{29}H_{50}O_3SSiNa$ ($[M+Na]^+$) 529.3148, found 529.3135.

(20R,22E,24R)-1α[(tert-Butyldimethylsilyl)oxy]-25-carbobutylsulfanyl-2-methylene-24-[(triethylsilyl)oxy]-26,27-cyclo-22-dehydro-19-norvitamin $D_3$ tert-butyldimethylsilyl ether (25)

To a stirred solution of 4 (37 mg; 64 μmol) in anhydrous tetrahydrofuran (1 ml) one drop of 1.7M solution of phenyllithium in di-n-butyl ether was added at −25° C. until a deep orange color persisted. A stoichiometric amount (34 μl; 58 μmol) of phenyllithium solution was then added. After 20 minutes, the mixture was cooled to −78° C. and a solution of 24 (22 mg; 43 μmol) in anhydrous tetrahydrofuran (400 μl) was siphoned via cannula. After 3 hours, the cooling bath was removed and the reaction mixture was stirred at 4° C. overnight. Then ethyl acetate (15 ml) was added and the mixture was washed with brine (3 ml). The organic phase was dried over anhydrous $MgSO_4$ and concentrated under reduced pressure. The residue was purified on a Waters silica gel Sep-Pack cartridge (0-5% ethyl acetate/hexane) to give 35 mg (40 μmol; 93% yield) of 25. UV (hexane) $\lambda_{max}$=245, 253, 263 nm; $^1H$ NMR (400 MHz, $CDCl_3$) δ 0.02 (3H, s), 0.05 (3H, s), 0.06 (3H, s), 0.08 (3H, s), 0.54-0.61 (9H, m), 0.86-0.95 (21H, m), 1.02 (3H, d, J=6.6 Hz), 1.96-2.07 (3H, m), 2.18 (1H, dd, J=12.4 Hz, J=8.4 Hz), 2.33 (1H, dd, J=13.1 Hz, J=2.7 Hz), 2.44-2.52 (2H, m), 2.82 (3H, m), 4.42 (2H, m), 4.80 (1H, d, J=7.4 Hz), 4.92 (1H, s), 4.97 (1H, s), 5.22 (1H, dd, J=15.3 Hz, J=7.4 Hz), 5.47 (1H, dd, J=15.3 Hz, J=8.9 Hz), 5.82 (1H, d, J=11.1 Hz), 6.21 (1H, d, J=11.1 Hz); $^{13}C$ NMR (101 MHz, $CDCl_3$) δ −5.1, −4.9, 5.0, 6.9, 12.2, 13.0, 13.6, 14.1, 2×18.2, 20.2, 22.0, 22.2, 23.4, 2×25.8, 27.9, 28.3, 28.7, 31.6, 38.5, 38.7, 40.3, 40.5, 45.6, 47.6, 55.9, 56.3, 70.9, 71.6, 72.5, 106.2, 116.1, 122.4, 128.0, 132.8, 139.0, 141.0, 152.9, 200.3; MS (EI) m/z 497 (15), 368 (13), 366 (13), 340 (14), 299 (70), 167 (79), 73 (100); exact mass (ESI) calculated for $C_{50}H_{90}O_4SSi_3Na$ ($[M+Na]^+$) 893.5765, found 893.5784.

(20R,22E,24R)-25-Carbobutylsulfanyl-2-methylene-26,27-cyclo-22-dehydro-1α,24-dihydroxy-19-norvitamin $D_3$ (26, AS-51)

Compound 25 was dissolved in a mixture of formic acid, tetrahydrofuran and water (500 μl; 6/3/1) at 0° C. The cooling bath was removed and the mixture was stirred for 20 hours. Saturated aqueous solution of $NaHCO_3$ (1.5 ml) was added carefully at 0° C. and the mixture was extracted with ethyl acetate (5×10 ml). The organic phase was dried over anhydrous $MgSO_4$ and concentrated under reduced pressure. The residue was purified on a Waters silica gel Sep-Pack cartridge (10-50% ethyl acetate/hexane) and on HPLC (5% 2-propanol/hexane; Zorbax Rx-Sil, 9.4 mm×25 cm, 5 μm column; 4 ml/min.; $R_t$=22.0 min.) to give 830 μg (1.6 μmol; 35% yield) of 26 (AS-51). UV (EtOH) $\lambda_{max}$=244, 252, 261 nm; $^1H$ NMR (500 MHz, $CDCl_3$) δ 0.56 (3H, s), 0.92 (3H, t, J=7.3 Hz), 1.04 (3H, d, J=6.6 Hz), 1.96-2.03 (2H, m), 2.08 (1H, m), 2.26-2.35 (2H, m), 2.57 (1H, dd, J=13.4 Hz, J=4.3 Hz), 2.81-2.87 (4H, m), 2.96 (1H, d, J=6.4 Hz), 4.18 (1H, m), 4.45-4.51 (2H, m), 5.09 (1H, s), 5.11 (1H, s), 5.37 (1H, dd, J=15.3 Hz, J=6.7 Hz), 5.54 (1H, dd, J=15.3 Hz, J=8.7 Hz), 5.88 (1H, d, J=11.1 Hz), 6.36 (1H, d, J=11.1 Hz); MS (EI) m/z 497 (2), 453 (2), 425 (4), 394 (4), 285 (21), 269 (28), 251 (37), 147 (47), 135 (100); exact mass (ESI) calculated for $C_{32}H_{48}O_4SNa$ ($[M+Na]^+$) 551.3171, found 551.3157.

1-Acetylcyclopropanecarboxylic acid methyl ester (28)

To a vigorously stirred suspension of anhydrous $K_2CO_3$ (40.0 g; 290 mmol) in acetonitrile (100 ml), tetra-n-butylammonium bromide (3.20 g; 10.0 mmol), 1,2-dibromoethane (13.0 ml; 28.4 g; 150 mmol) and methyl acetoacetate 27 (10.8 ml; 11.6 g; 100 mmol) were added. The reaction mixture was stirred for 4 days. The solids were filtered off and the filtrate was concentrated under reduced pressure. The residue was purified by distillation under reduced pressure to give 9.55 g (67.0 mmol; 67% yield) of 28. $^1H$ NMR (400 MHz, $CDCl_3$) δ 1.48 (4H, s), 2.47 (3H, s), 3.75 (3H, s); $^{13}C$ NMR (101 MHz, $CDCl_3$) δ 19.3, 29.8, 34.9, 171.5, 203.0; MS (EI) m/z 143 ($[M+H]^+$, 100), 142 ($M^+$, 70), 127 (81), 111 (87); exact mass calculated for $C_7H_{11}O_3$ ($[M+H]^+$) 143.0708, found 143.0705.

1-Acetylcyclopropanethiocarboxylic acid S-n-butyl ester (29)

To a stirred solution of 28 (6.80 g; 47.9 mmol) in methanol (40 ml) $LiOHxH_2O$ (1.05 g; 25.0 mmol) was added. After 3 days, 1M HCl solution in diethyl ether (25.0 ml; 25.0 mmol) was added dropwise at 0° C. Solvents were removed under reduced pressure and residual moisture was removed by evaporating with anhydrous toluene (3×30 ml).

The residue was dissolved in anhydrous methylene chloride (140 ml) and treated with N-hydroxysuccinimide (5.52 g; 48.0 mmol), 4-dimethylaminopyridine (293 mg; 2.40 mmol) and N,N'-dicyclohexylcarbodiimide (12.4 g; 60.0 mmol) for 6 hours. Then triethylamine (1.35 ml; 0.97 g; 9.60 mmol) and 1-butanethiol (25.6 ml; 21.6 g; 240 mmol) was added. After 2 days, volatiles were removed under reduced pressure and the residue was purified by column chromatography (2-8% ethyl acetate/hexane) to give 1.95 g (9.75 mmol; 20% yield) of 29. $^1H$ NMR (400 MHz, $CDCl_3$) δ 0.93 (3H, t, J=7.3 Hz), 1.40 (2H, m), 1.51 (4H, m), 1.56 (2H, m), 2.37 (3H, s), 2.91 (2H, t, J=7.4 Hz); $^{13}C$ NMR (101 MHz, $CDCl_3$) δ 13.5, 18.8, 21.9, 28.9, 29.0, 31.3, 43.8, 197.0, 202.5; MS (EI) m/z 201 ($[M+H]^+$, 15), 200 ($M^+$, 5), 173 (17), 145 (30), 116 (54), 111 (100); exact mass (ESI) calculated for $C_{10}H_{16}O_2SNa$ ($[M+Na]^+$) 223.0769, found 223.0764.

1-(2-Bromoacetyl)cyclopropanethiocarboxylic acid S-n-butyl ester (30)

To a stirred solution of 29 (1.90 g; 9.50 mmol) and triethylamine (2.67 ml; 1.92 g; 19.0 mmol) in anhydrous methylene chloride (80 ml) triethylsilyl trifluoromethanesulfonate (2.15 ml; 2.51 g; 9.50 mmol) was added dropwise at 0° C. After 30 minutes, a solution of N-bromosuccinimide (1.85 g; 10.4 mmol) in anhydrous methylene chloride was added via cannula and the cooling bath was removed. After the next 30 minutes, the solvent was removed under reduced pressure and the residue was purified by column chromatography (2-10% ethyl acetate/hexane) to give 1.58 g (5.66 mmol; 60% yield) of 30. $^1H$ NMR (500 MHz, $CDCl_3$) δ 0.95 (3H, t, J=7.4 Hz), 1.42 (2H, m), 1.60 (2H, m), 1.70 (4H, m), 2.94 (2H, t, J=7.4 Hz), 4.43 (2H, s); $^{13}C$ NMR (126 MHz, $CDCl_3$) δ 13.5, 21.1, 21.9, 28.9, 31.2, 34.4, 76.7, 196.9, 197.4; exact mass (ESI) calculated for $C_{10}H_{15}BrO_2SNa$ ($[M+Na]^+$) 300.9874, found 300.9879.

1-[2-(Dimethoxyphosphoryl)acetyl]cyclopropanethiocarboxylic acid S-n-butyl ester (19)

A solution of 30 (1.55 g; 5.56 mmol) and trimethylphosphite (0.85 ml; 0.90 g; 7.23 mmol) in toluene (20 ml) was refluxed overnight. Then the solvent was distilled off and the residue was purified by column chromatography (4-10% 2-propanol/hexane) to give 693 mg (2.25 mmol; 41% yield) of 19. $^1H$ NMR (400 MHz, $CDCl_3$) δ 0.93 (3H, t, J=7.3 Hz), 1.39 (2H, m), 1.57 (2H, m), 1.60-1.63 (2H, m), 1.68-1.71 (2H, m), 2.91 (2H, t, J=7.4 Hz), 3.61 (2H, d, $J_{H-P}$=22.0 Hz), 3.77 (6H, d, $J_{H-P}$=11.2 Hz); $^{13}C$ NMR (101 MHz, $CDCl_3$) δ 13.5, 20.5, 21.9, 39.5 (d, $J_{C-P}$=131 Hz), 44.0, 52.9 (d, $J_{C-P}$=6.8 Hz), 196.4 (d, $J_{C-P}$=6.0 Hz), 197.7; MS (EI) m/z 308 ($M^+$, 15), 290 (21), 251 (38), 221 (86), 219 (100); exact mass (ESI) calculated for $C_{12}H_{21}O_5PSNa$ ($[M+Na]^+$) 331.0745, found 331.0753.

Example 3: Biological Activity

Vitamin D Receptor Binding
Test Material
Protein Source

Full-length recombinant rat receptor was expressed in *E. coli* BL21(DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in $TEDK_{50}$ (50 mM Tris, 1.5 mM EDTA, pH 7.4, 5 mM DTT, 150 mM KCl) with 0.1% Chaps detergent. The receptor protein and ligand concentration was optimized such that no more than 20% of the added radiolabeled ligand was bound to the receptor.

Study Drugs

Unlabeled ligands were dissolved in ethanol and the concentrations determined using UV spectrophotometry ($1,25(OH)_2D_3$: molar extinction coefficient=18,200 and $\lambda_{max}$=265 nm; Analogs: molar extinction coefficient=42,000 and $\lambda_{max}$=252 nm). Radiolabeled ligand ($^3H$-$1,25(OH)_2D_3$, ~159 Ci/mmole) was added in ethanol at a final concentration of 1 nM.

Assay Conditions

Radiolabeled and unlabeled ligands were added to 100 mcl of the diluted protein at a final ethanol concentration of ≤10%, mixed and incubated overnight on ice to reach binding equilibrium. The following day, 100 mcl of hydroxylapatite slurry (50%) was added to each tube and mixed at 10-minute intervals for 30 minutes. The hydroxylapaptite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand.

HL-60 Differentiation

Test Material

Study Drugs

The study drugs were dissolved in ethanol and the concentrations determined using UV spectrophotometry. Serial dilutions were prepared so that a range of drug concentrations could be tested without changing the final concentration of ethanol (≤0.2%) present in the cell cultures.

Cells

Human promyelocytic leukemia (HL60) cells were grown in RPMI-1640 medium containing 10% fetal bovine serum. The cells were incubated at 37° C. in the presence of 5% $CO_2$.

Assay Conditions

HL60 cells were plated at $1.2\times10^5$ cells/ml. Eighteen hours after plating, cells in duplicate were treated with the drug. Four days later, the cells were harvested and a nitro blue tetrazolium reduction assay was performed (Collins et al., 1979; *J. Exp. Med.* 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

Antagonism was tested by adding a combination of $1,25(OH)_2D_3$ and the putative antagonist in the same well keeping the final ethanol concentration the same.

In Vitro Transcription Assay

Transcription activity was measured in ROS 17/2.8 (bone) cells that were stably transfected with a 24-hydroxylase (24OHase) gene promoter upstream of a luciferase reporter gene (Arbour et al., 1998). Cells were given a range of doses. Sixteen hours after dosing, the cells were harvested and luciferase activities were measured using a luminometer. RLU=relative luciferase units.

Intestinal Calcium Transport and Bone Calcium Mobilization

Male, weanling Sprague-Dawley rats were placed on Diet 11 (0.47% Ca) diet+AEK oil for one week followed by Diet 11 (0.02% Ca)+AEK oil for 3 weeks. The rats were then switched to a diet containing 0.47% Ca for one week followed by two weeks on a diet containing 0.02% Ca. Dose administration began during the last week on 0.02% calcium diet. Four consecutive intraperitoneal doses were given approximately 24 hours apart. Twenty-four hours after the last dose, blood was collected from the severed neck and the concentration of serum calcium determined as a measure of bone calcium mobilization. The first 10 cm of the intestine was also collected for intestinal calcium transport analysis using the everted gut sac method.

Antagonism was tested by administering a combination of $1,25(OH)_2D_3$ and the putative antagonist to the animal simultaneously.

Biological Activity Results (20R,22E)-2-Methylene-25-(4-methylpentanoyl)-24-oxo-26,27-cyclo-22-dehydro-1α-hydroxy-19-norvitamin $D_3$ (PP-48) shows lower affinity relative to $1,25(OH)_2D_3$ in binding to the recombinant vitamin D receptor as shown in FIG. 1 It is only about 10 less active than $1,25(OH)_2D_3$ in causing the differentiation of HL-60 cell in culture (FIG. 2). Likewise, it is about 10 times less active than $1,25(OH)_2D_3$ in increasing transcription of the 24-hydroxylase gene (FIG. 3). In vivo testing demonstrated that PP-48 displays essentially no ability to mobilize calcium from bone, even high doses (FIG. 4). However, its intestinal transport activity is similar to that of the native hormone, $1,25(OH)_2D_3$ (FIG. 5). The intestinal specific nature of PP-48 coupled with its cellular differentiation activity makes it a candidate for therapy in intestinal based diseases, such as Crohn's disease or celiac disease. Further, PP-48 should find utility in the treatment of secondary hyperparathyroidism of patients suffering from chronic kidney failure because it is undesirable to elevate serum calcium above normal in these patients for fear of calcification of heart, aorta and other vital organs while suppressing parathyroid gland proliferation and transcription of the preproparathyroid gene. Likewise, PP-48 should also be useful in the treatment of malignancy such as breast, colorectal and prostate cancers, or in the treatment of autoimmune diseases such as multiple sclerosis, lupus, rheumatoid arthritis, type 1 diabetes, and inflammatory bowel disease. PP-48 should also be useful in preventing transplant rejection, psoriasis, leukemia, host versus graft rejection, asthma, renal osteodystrophy, or osteoporosis. PP-48 should also be useful in treating skin conditions as wrinkles, lack of adequate skin firmness, lack of adequate dermal hydration, or insufficient sebum secretion.

Figure 7:
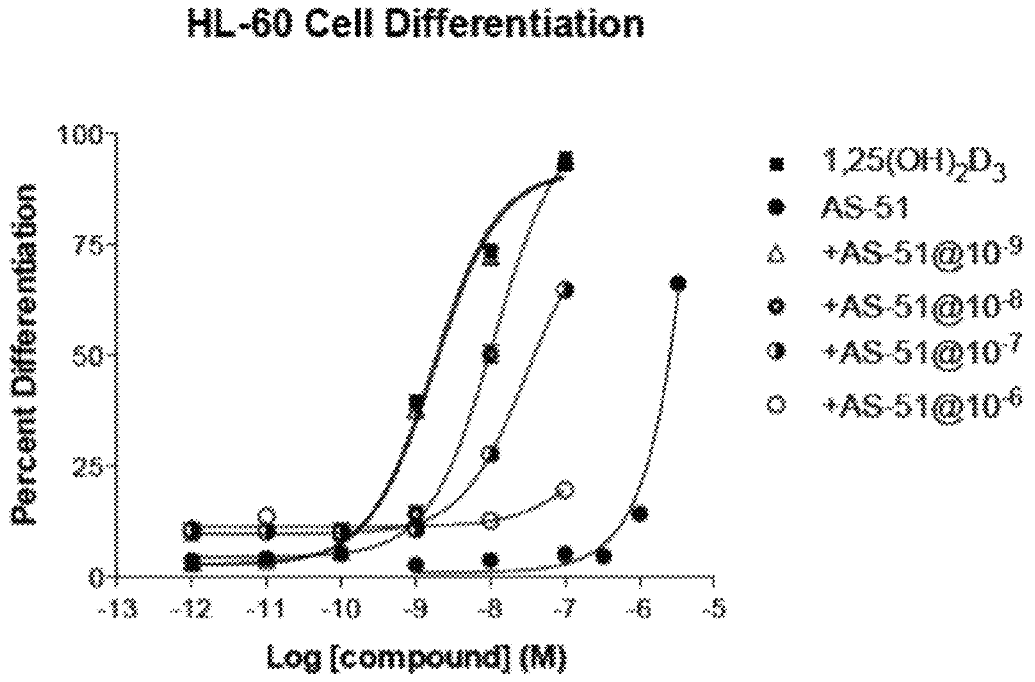
Figure 8:
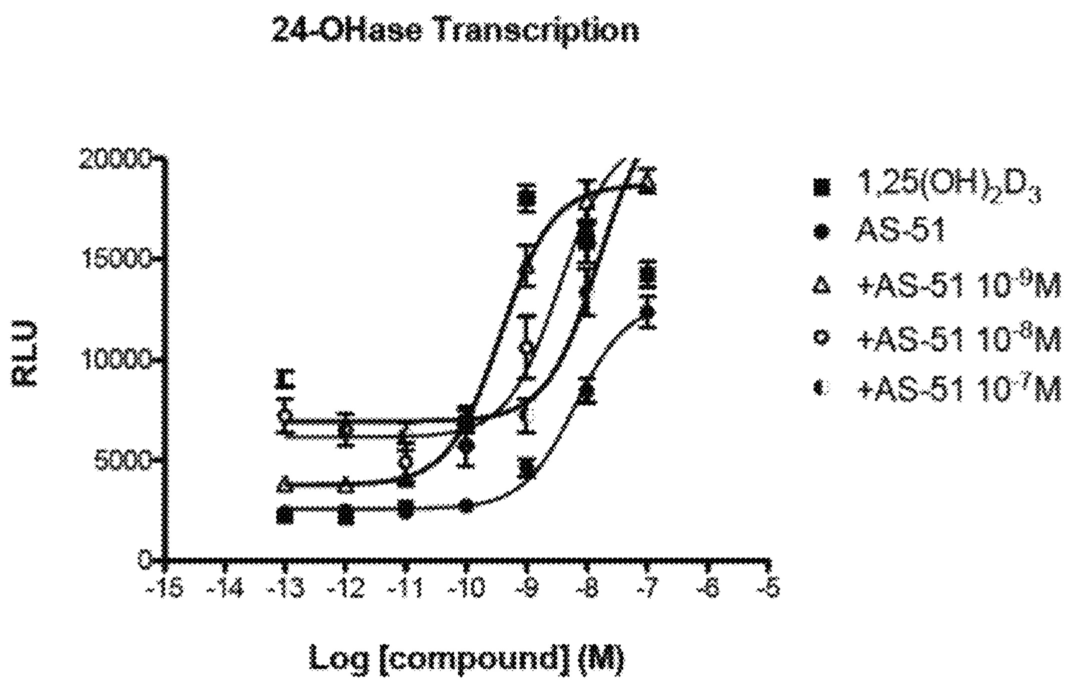

(20R,22E,24R)-25-Carbobutylsulfanyl-2-methylene-26,27-cyclo-22-dehydro-1α,24-dihydroxy-19-norvitamin $D_3$ (AS-51) competes for binding to the nuclear vitamin D receptor with the same potency as the native hormone (FIG. 6). In the HL-60 differentiation assay, AS-51 was found to be a potent inhibitor of the native hormone in causing the differentiation of HL-60 cells into monocytes (FIG. 7). In the 24-hydroxylase transcription assay, AS-51 was ~60 times less potent than $1,25(OH)_2D_3$ in causing 24-hydroxylase gene transactivation (FIG. 8). Notably, AS-51 can inhibit gene transactivation stimulated by the native hormone. In vivo testing of AS-51 indicated the derivative to be essentially inactive in releasing bone calcium stores (FIG. 9) and was somewhat less active than $1,25(OH)_2D_3$ in stimulating intestinal calcium transport at very high doses. When tested in combination with the native hormone, no antagonism was observed at the dose levels tested and using systemic administration. Thus, AS-51 is a fairly potent antagonist, as it shows inhibition of cellular differentiation and gene transactivation at concentrations of ~$10^{-8}$-$10^{-7}$ M. While in vivo testing indicates that AS-51 may not act as antagonist when given systemically, in vitro activities suggest AS-51 could be given locally and act in an inhibitory manner. In vivo use of such an antagonist would be useful in the treatment of diseases in which there is an excess of $1,25(OH)_2D_3$ production, such as sarcoidosis or as an antidote for vitamin D intoxication. AS-51 should also be useful in treating hypercalcemia.

Comparison to Other Compounds

Table 1 shows biological data for the compounds from the present disclosure (PP-48 and AS-51) in comparison to other (22E)-2-methylene-26,27-cyclo-22-dehydro-1α-hydroxy-19-norvitamin $D_3$ analogs: (22E)-(24R)-24-butoxy-25-carbobutoxy-2-methylene-26,27-cyclo-22-dehydro-1α-hydroxy-19-norvitamin $D_3$ (referred to as "CN-67" in Table 1) and (22E)-(24R)-25-carbobutoxy-2-methylene-26,27-cyclo-22-dehydro-1α,24-dihydroxy-19-norvitamin $D_3$ (referred to as "OU-72" in Table 1). The present compounds, PP-48 and AS-51, display surprising and unexpected bioactivity in comparison to the known compounds in a number of respects. For example, in contrast to both CN-67 and OU-72, each of which displays antagonistic activity in the HL-60 differentiation and 24-hydroxylase transcription assays, PP-48 displays agonistic behavior, despite structural similarities. PP-48 is more than 10 times more active than CN-67 in VDR binding (i.e., 0.17/0.015≈11). AS-51 displays antagonistic activity in the HL-60 differentiation and 24-hydroxylase transcription assays, like CN-67 and OU-72. However, the activity profile of AS-51 in these cell-based assays is essentially opposite to that of CN-67 and OU-72. In particular, the potency of AS-51 is markedly lower than that of either CN-67 (i.e., 0.002/0.06≈0.03) or OU-72 (i.e., 0.002/0.3≈0.007) in HL-60 cells, yet is markedly higher in potency than either CN-67 (i.e., 0.02/0.007≈3) or OU-72 (i.e., 0.02/0.01=2) in bone cells in the 24-hydroxylase transcription assay. Thus, a cell-specific difference exists between AS-51 and the other (22E)-2-methylene-26,27-cyclo-22-dehydro-1α-hydroxy-19-norvitamin $D_3$ analogs CN-67 and OU-72. Finally, AS-51 is nearly 70 times more active than CN-67 in VDR binding (i.e., 1.0/0.015≈67).

TABLE 1

| Working Example[1] | Where | Side chain | Competitive VDR Binding[2] (Relative Activity)[3] | HL-60 Differentiation[4] (Relative Activity)[3] | 24OHase Transcription[4] (Relative Activity)[3] |
|---|---|---|---|---|---|
| PP-48 | Present | 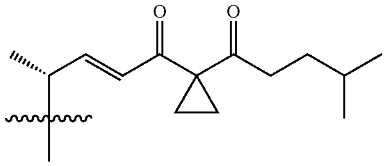 [SMILES: *[C@H](C)/C=C/C(=O)C1(C(=O)CCC(C)C)CC1] | 0.6 (0.17) | 30 (0.1) | 2 (0.1) |
| AS-51 | Present | 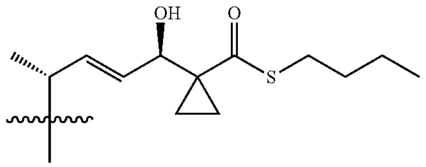 [SMILES: *[C@H](C)/C=C/[C@@H](O)C1(C(=O)SCCCC)CC1] | 0.1 (1.0) | >1000 (0.002) Antagonistic[5] | 6 (0.02) Antagonistic[5] |
| CN-67 | U.S. Pat No. 7,915,242 | 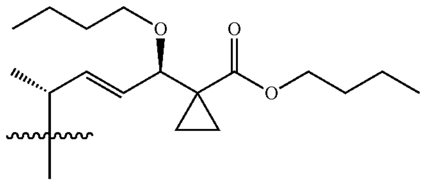 [SMILES: *[C@H](C)/C=C/[C@@H](OCCCC)C1(C(=O)OCCCC)CC1] | 1.5 (0.015) | 3 (0.06) Antagonistic[5] | 5 (0.007) Antagonistic[5] |
| OU-72 | U.S. Pat. No. 7,915,242 | 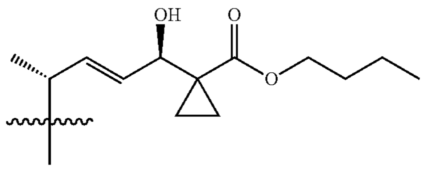 [SMILES: *[C@H](C)/C=C/[C@@H](O)C1(C(=O)OCCCC)CC1] | 0.023 (1.0) | 5 (0.3) Antagonistic[5] | 3 (0.01) Antagonistic[5] |

[1]All compounds are 2-methylene 19-nor compounds.

[2]$K_i$, nM.

[3]Relative to native hormone, $1,25(OH)_2D_3$ as measured in the same assay.

Relative activity = (value observed for native hormone)/(value observed for working example). Ratios less than one indicate the working example is less active than the native hormone.

[4]$EC_{50}$, nM.

[5]When administered with $1,25(OH)_2D_3$.

It is understood that the present technology is not limited to the embodiments set forth herein for illustration, but embraces all such forms thereof as comes within the scope of the following claims.

What is claimed is:

1. A compound of formula IV or a pharmaceutically acceptable salt thereof

IV

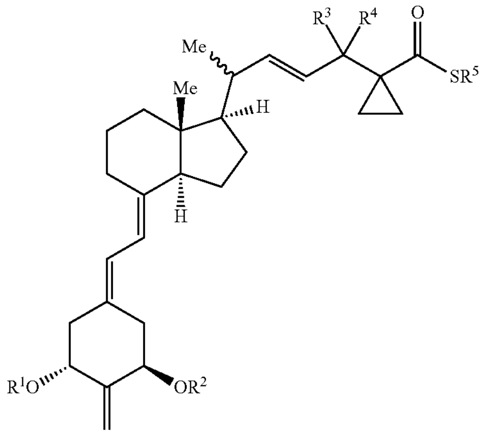

wherein $R^1$ and $R^2$ are independently selected from H and hydroxy-protecting groups selected from silyl protecting groups;

$R^3$ is $OR^6$ and $R^4$ is H, wherein $R^6$ is H or a hydroxy protecting group selected from silyl protecting groups; or $R^3$ and $R^4$ together represent a ═O group; and $R^5$ is a straight or branched chain alkyl group with 1 to 8 carbon atoms.

2. The compound of claim 1, wherein $R^3$ and $R^4$ together represent a ═O group.

3. The compound of claim 1, wherein $R^3$ is $OR^6$ and $R^4$ is H.

4. The compound of claim 3, wherein $R^6$ is H.

5. The compound of claim 1, wherein $R^1$ and $R^2$ are t-butyldimethylsilyl groups.

6. The compound of claim 1, wherein $R^1$ and $R^2$ are H.

7. The compound of claim 1, wherein $R^5$ is n-butyl.

8. A compound of claim 1, wherein the compound is of the formula VA, VB, VIA, VIB, VIC, or VID

VA

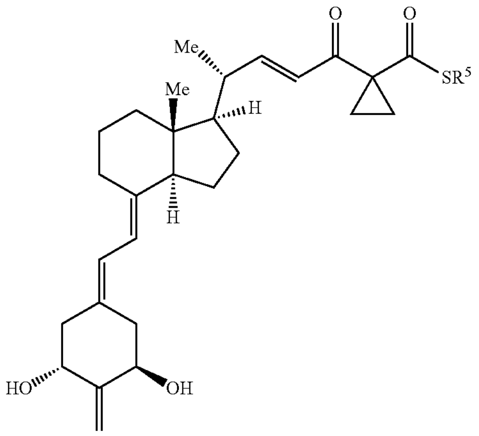

VB

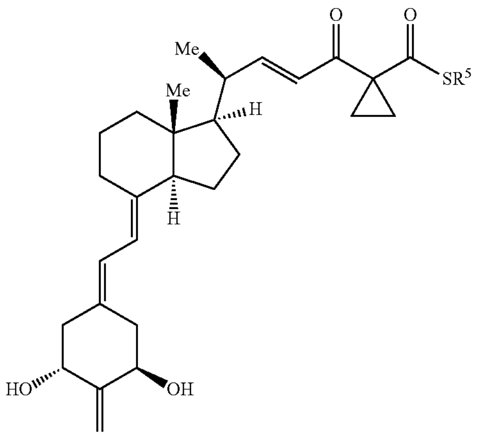

VIA

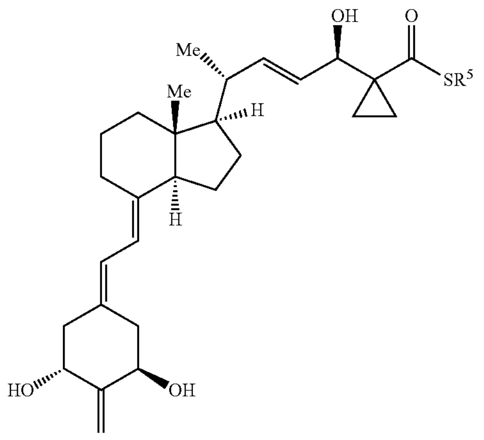

-continued
VIB
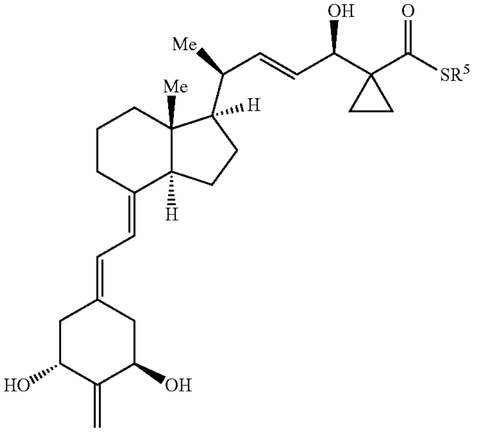
VIC
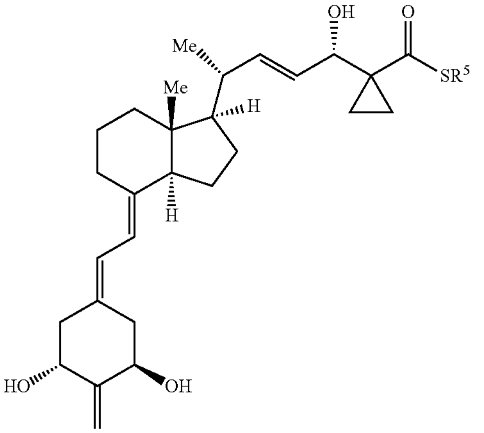
VID
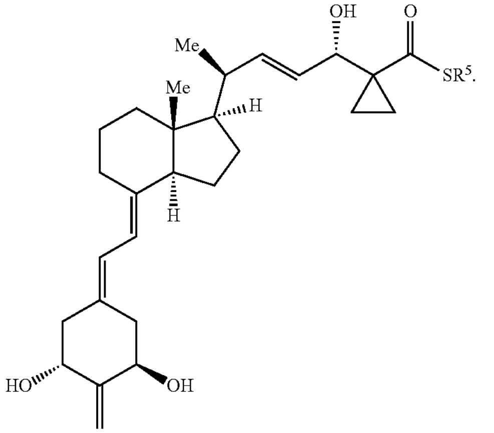
9. The compound of claim 1, wherein the compound is of the formula VIIA, VIIB, VIIIA, VIIIB, VIIIC, or VIIID
VIIA
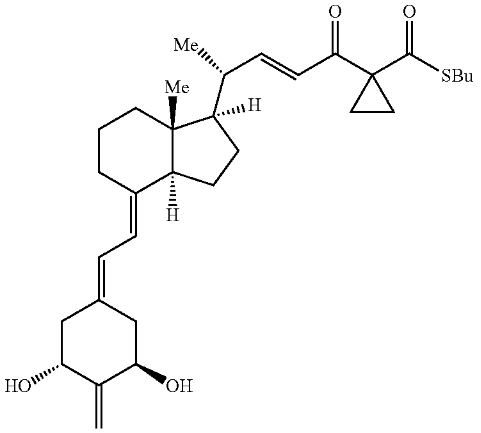
VIIB
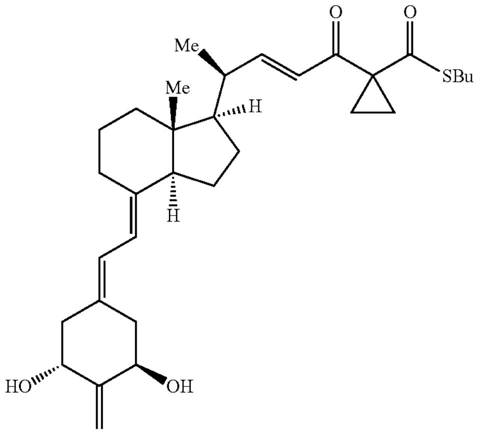
VIIIA
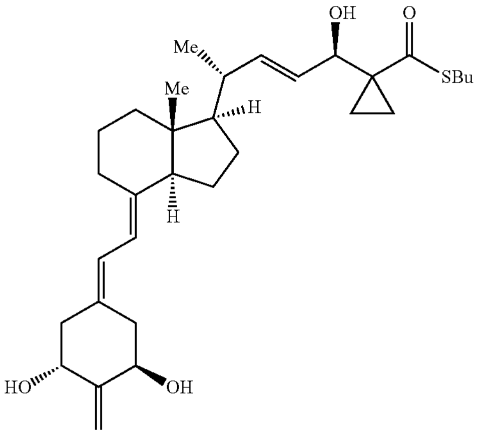

-continued

VIIIB

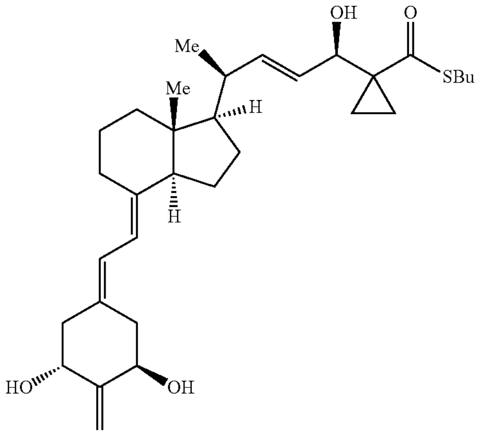

VIIIC

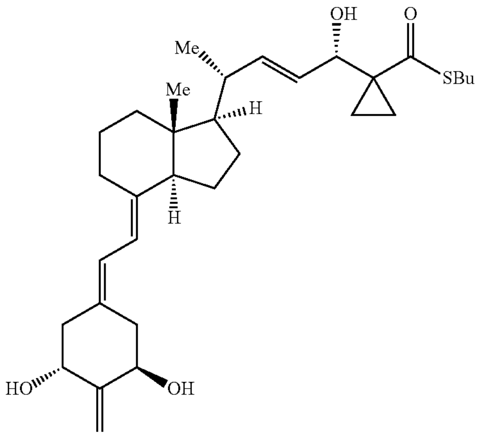

VIIID

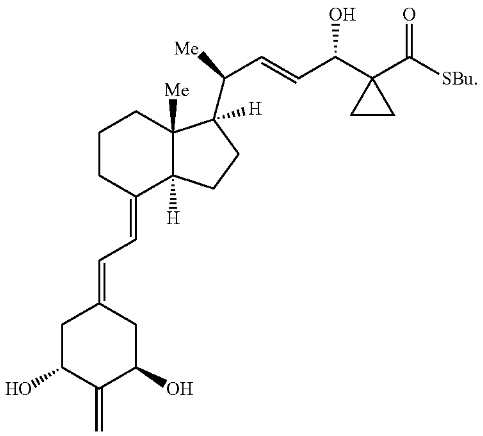

10. A pharmaceutical composition, comprising an effective amount of the compound of claim 8 and a pharmaceutically acceptable carrier.

11. The pharmaceutical composition of claim 10 wherein the effective amount is from about 0.01 μg to about 1 mg of the compound per gram of the composition.

12. The pharmaceutical composition of claim 10 wherein the effective amount is from about 0.1 μg to about 500 μg of the compound per gram of the composition.

13. A method of antagonizing the vitamin D receptor, comprising administering an effective amount of the compound of claim 8 or a pharmaceutical composition comprising an effective amount of the compound of claim 8 to a subject, wherein the compound administered to the subject antagonizes the vitamin D receptor.

14. The method of claim 13, wherein the compound or composition is administered orally, parentally, rectally, transdermally, or topically.

15. The method of claim 13, wherein the compound or composition is administered by delivering the compound or pharmaceutical composition in an aerosol.

16. A method of treating a biological condition comprising administering an effective amount of the compound of claim 8 or a pharmaceutical composition comprising an effective amount of the compound of claim 8 to a subject suffering from a biological condition selected from the group consisting of hypercalcemia, hyperparathyroidism, sarcoidosis, and vitamin D intoxication.

* * * * *